United States Patent [19]
Aiken et al.

[11] Patent Number: 5,256,538
[45] Date of Patent: Oct. 26, 1993

[54] DETECTION OF EARLY PLATELET ACTIVATION AND PREDIAGNOSIS OF THROMBOTIC EVENTS

[75] Inventors: Martha L. Aiken; Richard G. Painter, both of Tyler, Tex.

[73] Assignee: Board of Regents, The University of Texas System, Austin, Tex.

[21] Appl. No.: 668,272

[22] Filed: Mar. 8, 1991

[51] Int. Cl.$^5$ .............................................. C12O 1/00
[52] U.S. Cl. ...................... 435/7.9; 435/7.1; 435/7.21; 436/536; 436/548; 436/63; 436/69; 436/87; 514/56; 514/520
[58] Field of Search ............... 436/503, 536, 548, 63, 436/69, 87; 435/7.9; 514/56, 520

[56] References Cited

U.S. PATENT DOCUMENTS 4,610,960  9/1986  Mosher .
4,820,505  4/1989  Ginsberg .

OTHER PUBLICATIONS

Young et al.—Trans. Am. Soc. Artif. Intern. Organs (1982) vol. 28, pp. 498–503.
Jaffe et al. (1982), *Nature,* (London, England), 295(5846):246-8.
Wencel et al. (1984), *Am. J. Path.* (USA), 115(2):156-64.
Legrand et al. (1988), *Eur. J. Biochem.,* 171(1-2):393-9.
Aiken et al. (1987), *Blood* (USA), 69(1):58-64.
Aiken et al. (1986), *J. Clin. Invest.* (USA), 78:1713-1716.
Aiken et al. (1987), *Seminars in Thrombosis and Haemostasis,* 13(3):307-316.
Wolff et al. (1986), *J. Biol. Chem.* (USA), 261(15):6840-6.
Aiken, et al. (1990) *Blood,* 76:(12):2501-2509.
Silverstein et al. (1987), *J. Clin. Invest.* (USA), 79(3):867-74.
McCrohan et al. (1987), *Thromb. Haemostasis,* 58(3):850-2.
Abrams et al. (1990), *Blood,* 75:128-138.
Tuszynski et al. (1988), *Blood,* 72(1): 109-115.
Kao et al. (1986), *Am. J. Clin. Pathol.* (USA), 86(3):317-23.
Fuchs et al. (1987) *Am. J. Cardio.,* 60:5334–5337.
Saniabadi et al. (1986) *Thrombosis and Haemostasis,* 56(1):45-49.
Goodman and Gilman (1985) In: *the Pharmacological Basis of Therapeutics* 7th edition, pp. 1338-1362.
Frink et al. (1988) *Br Heart J.,* 59:196-200.
Lahav, J. (1988) *Blood,* 71(4):1096-1099.
Johnston et al. (1987) *Blood,* 69(5):1401-1403.
Coon, William W. (1976) *Ann. Surg.,* 186(2):149-164.
Kieffer, et al. (1988) *Biochimica et Biophysica Acta,* 967:408-415.
Gershlick, A. H. (1990) *Circulation,* 81(1):I-28-I-34.
Brown, et al. (1980) *Clinica Chimica Acta,* 101:225-233.
Plow, et al. (1986) *Proc. Natl. Acad. Sci. USA,* 83:6002-6006.
Patent Cooperation Treaty International Search Report, dated Aug. 19, 1992, application PCT/US 92/01757.

*Primary Examiner*—Sam Rosen
*Attorney, Agent, or Firm*—Arnold, White & Durkee

[57] ABSTRACT

The present invention relates to a highly sensitive diagnostic/prediagnostic test to identify persons at risk of a thrombotic event. Thrombotic events include myocardial infarction, deep venous thrombosis, pulmonary embolism, thromboembolic stroke pulmonary embolism deep venous and cardiovascular disease. The test is based on the early detection of elevated levels of resting platelet surface thrombospondin. The present invention also includes methods of determining the presence of thrombospondin on the surface TSP receptors of resting platelets in a biological sample. An anti-thrombospondin monoclonal antibody which is specific for thrombospondin on resting platelets is also disclosed. A diagnostic test in the form of a test kit for the determination of thrombospondin levels in a patient sample, and also for the prediagnosis of persons at risk for thrombotic events, is also described.

31 Claims, 10 Drawing Sheets

180K—

1 2 3 4 5 6

DETECTION OF EARLY PLATELET ACTIVATION AND PREDIAGNOSIS OF THROMBOTIC EVENTS

The government may own rights to the present invention as relevant research was funded by NIH grant HL39702.

BACKGROUND OF THE INVENTION

1. Field of the Invention

The present invention relates to the field of thrombotic disorders and diagnostic tests to predict their onset. More specifically, the present invention relates to the field of early diagnostic tests for the prediction of thrombotic events such as myocardial infarction, thromboembolism, stroke and related conditions.

In that the method whereby these thrombotic events are predicted is based on the presence of thrombospondin on the surface of a very small number of activated cells and more importantly a much larger number of resting platelets, the present invention relates to methods of analyzing resting platelets and their associated molecules. More specifically, the present invention relates to methods of analyzing resting platelets to qualitatively and quantitatively measure thrombospondin present on TSP receptors on the surface of resting platelets in a biological sample. Most specifically, the present invention relates to the field of determining thrombospondin concentrations as present on the population of resting platelets in a biological sample.

The invention also relates to the field of monoclonal and polyclonal antibodies, more particularly, a specific monoclonal antibody capable of immunologically binding with thrombospondin present on the surface of resting platelet surface TSP receptors is most preferably used in the described diagnostic and predictive methods.

As the present invention relates generally to the field of method for monitoring slight increases in platelet activation the described invention also relates to methods by which the effects of anti-thrombotic regimens in post-thrombotic patients can be evaluated and monitored in the patient. The present invention also relates to the field of post-thrombotic event monitoring systems, as the present techniques can also be used to determine if post-thrombotic resting platelet TSP concentrations have returned to "normal" or pre-thrombotic levels.

The present invention also relates to the field of diagnostic kits, as a particular diagnostic kit for use in the screening of biological samples to determine persons at risk of a thrombotic event is disclosed. The prediction of a thrombotic event is accomplished by the inclusion in the diagnostic kit of a monoclonal or polyclonal antibody (or Fab fragment thereof) which is capable of binding thrombospondin on resting platelets. In the disclosed diagnostic test, elevated levels of antibody binding to resting platelets indicate a person at potential risk of a thrombotic event.

2. Description of the Related Art

Cardiovascular disease presents a serious health risk throughout the world and is the leading cause of death in the United States. According to the American Heart Association, as of 1988, 6.08 million Americans suffered from coronary disease, while as of this year an additional 2.93 million Americans suffered from the devastating after effects of stroke. During 1988, a less fortunate 150,300 Americans died of stroke, while 511,050 died of coronary heart failure. More than 300,000 people a year die of heart attack prior to reaching a medical facility.[36] These statistics clearly support the need for a clinical test to identify these individuals before a major thrombotic event occurs.

In addition to these distressing statistics, the estimated cost of cardiovascular diseases in 1991 in terms of health care and medication in the United States alone was estimated to be about 101.3 billion dollars. An itemized analysis of these costs reveals that only 5.4 billion dollars (less than 6% of the total estimated expenditures) was related to the cost of medications in treating these conditions, while the remainder relates to costs associated with hospitalization, nursing care and lost output.[36] Clearly, these figures reflect that the current clinical management of these conditions is through the treatment of post-event symptoms, rather than through regimens to prevent or reduce the severity of an oncoming thrombotic event.

One reason for the lack of emphasis on clinical techniques for the prevention of a thrombotic event is the clinical inadequacy of current methods to timely indicate an oncoming thrombotic event. Generally, there are no symptoms preceding a damaging thrombotic event, such as a thrombogenic stroke. Some limited platelet activation has been reported to preclude myocardial infarction, thrombotic stroke, and deep venous thrombosis.[4, 5, 17, 33, 34, 36, 42, 47, 48] Therefore, several techniques proposed for detecting platelet activation have included the monitoring of platelet-secreted proteins, such as the several platelet proteins.[47, 42, 4, 49, 50]

Methods for examining the thrombotic event have been developed based on particular "marker" proteins, most specifically, proteins present on the surface of activated platelets.[47, 42, 4, 49, 50] However, the opportunity to clinically intervene in time to preclude thrombus formation is often lost by the time the concentration of activated platelets in the circulation reaches detectable levels.

An analysis of particular platelet proteins contemplated as potential "markers" of platelet activation and/or pre-indicators of thrombotic events requires their individual evaluation in light of the following criteria:

1. Clearance Time—The compound should not be rapidly cleared from the system being monitored.
2. Measurability—The compound should be accurately measurable.
3. Specificity—The compound must be specific for indicating an imminent increase in platelet activation, and hence onset of thrombus formation is soon to occur in vivo.

Once platelets become activated, they do not enjoy a normal intravascular survival. The decreased intravascular survival of activated platelets tends to also decrease the sensitivity of an assay directed at the circulating activated platelets themselves.[57, 58]

Several of the proposed platelet "marker" proteins are released as a consequence of the particular condition of the patient (diseased vs non-diseased state) and the particular handling and sampling techniques used in obtaining the sample.[47, 42, 4, 49, 50] For example, βTG and PF4 are two platelet proteins which are released as a consequence of limited platelet activation, but these molecules are rapidly cleared from the circulation and a good correlation between elevated levels of these proteins in plasma and pre-thrombotic conditions has not been established.[47, 42, 4, 49, 50]

Other adhesive platelet proteins, such as fibrinogen,[37, 38] von Willebrand factor and fibronectin, bind only to GPIIb/IIIa complex present on the surface of physiologically "activated" platelets.[8, 59, 6, 64, 24, 60, 61, 62, 63, 65, 66]

Antibodies directed against activated platelet secreted proteins are typically used to detect surface proteins via radioimmunoassay. Expression of these and other adhesive proteins on the platelet cell surface occurs upon platelet stimulation and secretion of alpha granule components. By way of example, particular proteins which are secreted by activated platelets include fibrinogen, fibronectin, von Willebrand factor, beta-thromboglobin ($\beta$TG), platelet factor 4 and thrombospondin.[17, 33, 34, 36, 47, 42, 5, 48, 4, 49, 50, 8, 59, 6, 64, 24, 60, 61, 62, 63, 65, 66] Some of the secreted proteins appear on the surfaces of the small number of activated platelets while others are rapidly cleared from the circulation. Of these proteins, only thrombospondin is known to interact with not only the limited number of activated cells (which are likely to be cleared from the circulation by adhering to the endothelium), but also the larger population of circulating non-activated platelets.[67, 68, 69, 70, 71]

While the GP11b/IIIb complex is present on both resting and activated platelets, these two components form a functional (i.e., able to support the binding of adhesive proteins to the platelet surface) "binding" site only when the platelet is in an activated state.[72, 73] Earlier studies have not been successful in detecting this very limited number of cells prior to thrombosis. A further deterrent to the measurement of activated platelets is due to the adhesive properties of activated cells which result in their rapid clearance from the circulation due to platelet aggregation and interaction with damaged endothelium.[57, 58] Thus, use of these particular platelet proteins as "markers" or "predictors" of thrombosis is not sufficiently sensitive enough to signal slight increases in platelet activation, or the beginnings of an imminent thrombotic event.

Although the degree of platelet adhesiveness has been correlated to the degree of thrombotic risk (Shaw, 1967), or with the incidence of thrombotic disease (Bygdeman, 1969), it has not been possible to predict whether an individual falls into a particular "high" risk group through monitoring platelet "adhesive" proteins. Primarily, the lack of sensitivity of the above "marker" proteins which are found only in association with the small population of activated platelets (due to the reasons cited above) make such measurements unreliable. In addition, such measurements are subject to considerable variability.[13]

The Ginsberg patent describes a method for detecting activated platelets using an imaging reagent monoclonal antibody capable of binding thrombospondin expressed on the surface of activated platelets.[22] Specifically, the Ginsberg patent focuses on the detection of relatively large thrombi consisting of platelet aggregates within the body after the intravenous introduction of the radioactive imaging reagent monoclonal antibody into the patient. Clearly such a relatively invasive method, while of value in detecting the location of large thrombi in post-thrombotic patients, would have little value as a convenient non-invasive, predictive methodology. The relatively low resolution and sensitivity of the imaging techniques employed would preclude detection of thrombospondin on the circulating population of resting platelets as well as small, nascent platelet aggregates that would be expected in pre-thrombotic patients. Currently, the inability to detect platelet activation early in the pre-thrombotic stage often results in the loss of an opportunity to effectively intervene clinically to halt exponential platelet activation and thrombi formation.

Assay methods used to monitor activated platelets include standard radioimmunoassay for proteins released into the plasma by activated platelets and flow cytometric immunological detection of activated platelets utilizing fluorescently labeled antibodies which interact specifically with the activated cell population.[17, 33, 34, 36, 47, 42, 5, 48, 4, 49, 50, 8, 59, 6, 64, 24, 60, 61, 62, 63, 65, 66]

Moreover, methods which rely on the analysis of activated platelets suffer from a lack of sensitivity due to the removal of activated platelets from the circulation. Activated platelets have adhesive qualities which mediate interactions with damaged endothelium and atherosclerotic plaques.[57, 58] As an example, a recent study attempted to detect activated platelets in blood samples from nine patients undergoing cardiopulmonary bypass surgery.[29] This study employed flow cytometry. Three antibodies specific for activated platelets were used. One antibody was specific for fibrinogen associated with the activated platelet surface. This antibody gave positive results with only 2 of the 9 patients. The second antibody recognized GMP-140 which becomes expressed on the surface of activated platelets. This antibody gave positive results for only 1 of the 9 patients. A third antibody (PAC-1) directed against the active form of the fibrinogen receptor, GPIIb-IIIa, was positive in 5 out of 9 patients. It was also reported that the interaction of the anti-GMP-140 (S12) with activated platelets decreased when the cells were fixed with paraformaldehyde. This was also true for the PAC-1 antibody.

The above complication required the samples to be analyzed immediately to avoid spontaneous activation of the platelets which would invalidate the results. This would be cumbersome at best and most likely impossible in a clinical setting. Even if the samples could be processed quickly enough, the lack of sensitivity even under the most favorable conditions would make these procedures useless in detecting limited platelet activation which occurs prior to a thrombotic event.

In addition, these investigators measured the increase in platelet-derived microparticles and found a 2-fold increase, but could not definitely correlate this observation with increased platelet activation due to the surgery as opposed to the mechanical shear factors involved. As these blood samples were taken directly from an access port in the bypass circuit with little or no opportunity for the activated cells to be cleared (it is possible that some of the activated cells adhered to the bypass circuit itself), these results are not promising.

It is clear that the above methods are not adequate to detect platelet activation under extreme conditions, much less the limited activation that would precede a thrombotic event. In addition, methods which rely on the detection of proteins secreted into the circulation are equally unreliable. In large part, this unreliability is due to the rapid clearance rate of these proteins[13]. Another contributing factor is the large variability in the established normal range of concentrations of these proteins in the plasma.[13]

Detection and measurement methods which in general depend on activated platelets are therefore unreliable because of: (1) endothelial removal of activated platelets; (2) lack of sufficient sensitivity and/or "signal-to-noise" ratio necessary to detect the small percentages of activated platelets that are present; (3) large variability in established normal ranges; and (4) in some procedures, the requirement to process samples immediately is unfeasible.

Thrombospondin is now known to be synthesized by a variety of cells including megakaryocytes, endothelial cells, smooth muscle cells, fibroblasts, monocytes and macrophages.[6, 8] Thrombospondin resides primarily in endogenous pools within the alpha-granules of platelets, and unlike other platelet proteins, is present in very low concentrations in plasma (20–165 ng/ml in blood plasma).[8]

The capacity of thrombospondin to interact with resting cells makes it unique among the platelet adhesive glycoproteins.[8] In comparison to other platelet proteins, the concentration of thrombospondin has been reported to be 3 to 5 orders of magnitude *less* than fibronectin or fibrinogen blood plasma levels.[8] The low levels of TSP associated with resting platelets is also consistent with detectable plasma levels of thrombospondin.

Thrombospondin is known to have functional surface receptors on both activated and resting platelets.[8] A substantial body of evidence suggests that TSP is either absent, or only present at minimal levels, on the surface of resting platelets.[6, 8] As already noted, blood platelets mobilize certain cytoplasmic storage granules (alpha granules) upon "activation". These alpha granules release thrombospondin into the extracellular environment upon platelet activation. TSP then binds TSP receptors located on activated platelet surfaces. Released thrombospondin also binds to non-stimulated or resting platelets at a separate population of high affinity TSP surface receptors.[43] The binding affinity of endogenous thrombospondin for resting platelets is particularly high, with a Kd less than 4 nM, the binding affinity between the activated platelet receptor and thrombospondin has been estimated at 250 nM.[7] At the normal plasma concentration of TSP, which has been estimated to be as high as 20 to 165 ng/ml[8], it has been predicted that there may exist from 30 to 225 molecules of TSP on the surface of a resting platelet.[7, 8]

A resting platelet contains approximately 3,000 high-affinity receptor sites on its surface at which TSP can bind.[3] Thus, the binding of thrombospondin to resting platelets is described as having a low-capacity mechanism, in that resting platelets are capable of binding a maximum of 3000 molecules of thrombospondin per resting platelet cell.

In contrast, an activated platelet contains approximately 36,000 low affinity receptor sites on its surface at which TSP can bind. Thus, the interaction of thrombin-stimulated platelets (i.e., "activated" platelets) is characterized as having a lower affinity ($kd = 250$ nM) and high capacity.[8]

In contrast, many other platelet proteins proposed as potential "markers" of thrombosis are normally present at very high concentrations in the circulation (e.g., fibrinogen). A high relative plasma concentration of a particular protein would make it difficult to detect small changes in that particular protein concentration. Additionally, fibrinogen is difficult to detect on the surface of platelets. Specifically, the number of platelets which interact with fibrinogen is small, making the detection of platelets with surface-expressed fibrinogen difficult, if not impossible. Other proteins (e.g., $\beta$TG), while not normally present at high plasma concentrations, are cleared from the system, so rapidly that it becomes impossible to accurately relate elevated plasma levels with low level platelet activation.[74, 75, 76, 77, 78, 79]

Thus, both rapidly cleared, or high plasma concentration platelet proteins are rendered unreliable as in vivo thrombotic event indicators.

Since platelet activation is a preliminary event to thrombosis, the probability of which exponentially increases following injury to blood vessels and soft tissues, it is important to develop methods by which the onset of early platelet activation may be accurately predicted, particularly at low "activated" platelet concentrations. A system which was capable of predicting the onset of early platelet activation would aid in the prediction of those patients at risk of a thrombotic disorder. Most preferably, a sensitive and specific method for identifying a "prethrombotic state" would be relatively independent of the particular concentration of activated platelets in the circulation. Such would allow early thrombus detection, prior to the beginning of exponential platelet activation, and thereby increase the probability of halting an oncoming thrombotic event.

Such a method would also be useful in post-thrombosis treatment evaluations to determine the effectiveness of prescribed therapy. Current methods of post-thrombosis treatment evaluation monitor only blood fibrinopeptide thrombus breakdown products. Several post-thrombus therapies act to inactivate (maintain in a resting state) the platelets, and typically reduce future thrombus formation triggered by limited platelet activation.[40] However, this method does not measure platelet activation directly, thus, it cannot determine if a specific regimen is effective enough to prevent future thrombus formation.

As thrombotic events, such as myocardial infarction, thrombotic stroke, and deep venous thrombosis, occur without preceding symptoms other than limited, relatively undetectable platelet activation, a particular need exists for the development of a non-invasive, rapid clinical method for reliably predicting the onset of thrombosis. Similarly, a need also exists for an in vivo screening method for detecting persons at risk for such thrombotic events so as to provide more clinically effective thrombosis-preventive therapies. This screening method would also be extremely useful for monitoring the effectiveness of post-thrombotic therapies.

SUMMARY OF THE INVENTION

The present invention presents an easy to use and highly sensitive diagnostic test for predicting those persons at risk of a thrombotic event. This diagnostic test may be used to alert clinicians to a patient's need for a thrombosis-preventative pharmaceutical regimen. The disclosed methods and therapies are essentially independent of the actual concentration of activated platelets in a given sample, and therefore provide the most reliable predictor of thrombus formation heretofore available or contemplated.

The present inventive methods provide the means by which effective clinical intervention to halt thrombosis may be provided. Specifically, thrombotic events may be prevented or reduced in severity through the administration of anti-thrombotic pharmacological agents to patients pre-diagnosed to be at thrombotic risk. Such would spare millions the pain, suffering, and irreparable tissue damage which typically follow a thrombotic episode. Additionally, such a test would negate the current expenditure of billions of dollars in the hospitalization and related heath care support costs of coronary and stroke patients. Specifically, economic costs would be reduced and/or are eliminated altogether by avoiding the need for medical and nursing care typically required by persons recovering from heart attack or stroke.

The present invention as a predictor of thrombotic events may be used together with various antithrombotic pharmaceutical agents to effectively prevent and provide early treatment to dissipate an imminent thrombotic event. A preventative pharmaceutical regimen may include the administration of antithrombotic pharmacological agents, for example, aspirin (acetylsalicylic acid), heparin, or other anti-thrombotic pharmaceutical, to the person identified to be "at risk" of a thrombotic event.[40]

The population of platelet receptors for thrombospondin which exist on the surface of resting platelets has an especially high affinity for low concentrations of thrombospondin. The number of thrombospondin molecules that these receptors subsequently support in association with the resting platelet is typically between 30-225 molecules TSP per resting platelet. A second population of platelet TSP receptors exist only on the surface of physiologically "activated" (i.e., thrombin-stimulated) platelets, and have a relatively high capacity (supporting the binding of 36,000 molecules of thrombospondin per activated platelet) and lower binding affinity ($k_d = 250$ nM).[8]

The Inventors have found that monitoring the molecules of thrombospondin which exist in association with low capacity, high affinity resting platelet TSP receptors is especially well suited as a marker for detecting early platelet activation in vivo. More specifically, Inventors postulate that monitoring the amount of thrombospondin on resting platelets in a sample will predict the onset of exponential platelet activation and thrombus formation.

The Inventor's data supports the hypothesis that a method which monitors resting platelet-associated thrombospondin would be reasonably predictive of a thrombotic event in vivo taken together with the date provided herein when considered by those of skill in the art given that early platelet activation is known to be accompanied by the release of thrombospondin from activated platelet α-granules. While the small number of circulating "activated" platelets early in thrombosis is difficult to detect, the Inventors have observed that released thrombospondin binds to the described high affinity, low capacity TSP receptors on a large population of resting platelets. Small amounts of released thrombospondin from activated platelets anywhere within the circulation, thus results in a significant increase in the number of detectable resting circulating platelets with surface-associated thrombospondin molecules.

The number of the cell type (i.e., resting platelets) to be monitored in the presently disclosed system therefore becomes a non-limiting factor in the described assay methods. Additionally, since the claimed methods monitor a limited number of TSP receptors on a large number of resting platelets, a more sensitive method for indirectly indicating the presence of activated platelets results.

With the knowledge that early platelet activation is accompanied by an increase in resting platelet-associated thrombospondin, and the knowledge that resting platelets do not have functional surface receptors for any other platelet protein known to be released upon platelet activation (e.g. no functional resting-platelet receptors for fibrinogen, van Willebrand factor, fibronectin, and platelet factor 4), the Inventors determined that thrombospondin would be the "marker" protein of choice in screening patient blood samples for pre-thrombotic physiological events. The Inventors recognized that a system which was able to monitor changes in resting platelet-associated thrombospondin would both directly indicate an imminent exponential platelet activation phase while comprising a monitoring system which was independent of the concentration of activated circulating platelets. It is therefore also not necessary that the antibody be essentially free of binding affinity for activated platelets.

One particularly preferred embodiment of the method comprises for monitoring thrombospondin associated with resting platelets by using a monoclonal antibody capable of binding thrombospondin or resting platelets. Most preferably, the monoclonal antibody is F19D2, which is produced by a hybridoma ATCC # HB10516. A detection reagent, such as fluorescent 1 micron beads coated with protein-A (NEN, Boston, MA), may then be used to detect resting platelet-antibody complexes. The cells (resting platelets-antibody complex) with beads attached will be detected by flow cytometric analysis.

Most preferably, the platelets are fixed, for example, in paraformaldehyde,[7] before use in the detection techniques (flow cytometry, RIA, magnetic head assay) to broaden the applicability of the described assay. In this way, platelet thrombospondin levels need not be determined immediately upon drawing the sample to avoid spontaneous platelet activation and/or other platelet changes.

While resting platelets may be distinguished from activated platelets by flow cytometry, it is not critical to do so. The crux of these experiments is to show that more of the platelet cells in a sample are positive for TSP than there are activated cells in a sample. In clinical samples this will not be an issue at all because, as stated above, activated platelets themselves are not detectable in human blood samples. Thus, all cells are analyzed.

The use of flow cytometry in analyzing activated platelet surface proteins with fluorochrome-labeled antibodies is generally described by Abrams et al. (1990).[13] This reference is specifically incorporated herein by reference for the purpose of generally describing the process of flow cytometry in the basic flow cytometric analysis of activated platelets.[13] However, the Abrams et al. procedure requires that there exist at least 0.8% activated platelets in the circulation sample.[13] The procedure therein therefore was modified before it could provide the highly sensitive detection assay claim even in the presence of as little as 0.2% activated platelets in the circulation of the patient being treated.

Most significantly the flow cytometer according to the present methods must be adjusted to detect resting platelets which are positive for TSP (these cells will have antibody and fluorescent protein-A coated beads attached), and exclude debris and the free protein-A coated fluorescent beads which are close in size to the platelets. This is accomplished by labelling cells for filamentous actin (F-actin) (not present in beads), and measuring the relative green fluorescence of only the F-actin-positive population.[80]

Particular adjustments will vary between flow cytometers, and are adjustments well within the skill of the worker in the art of flow cytometry. Following these adjustments, a box (bitmap) is drawn around the cell population of interest which instructs the machine to ignore signals from other populations (free beads or debris). Measurements of the relative fluorescent intensity of the population are then made on either a linear or log scale.

While flow cytometry is a particularly preferred method for quantifying resting platelet-associated thrombospondin, other methods, such as the use of IgG-coated magnetized beads may be used to provide an effective resting platelet thrombospondin monitoring system. Moreover, standard antibody-antigen radiolabelled ligand binding techniques are also suitable for the monitoring of resting platelet-associated thrombospondin.[7] Thus, the present invention may be practiced by any of at least three different laboratory techniques: radiolabelled ligand binding assay; magnetic bead assay; and flow cytometry techniques.

While not intending to be limited to any theoretical mechanism of action in the described invention, the Inventors postulate the sensitivity of the described predictive detection techniques is in part attributable to the recognition and utilization of the phenomenon which exists between activated (stimulated) platelet secretion and resting platelet binding of thrombospondin in vivo, and the monitoring of this phenomenon through detecting elevated levels of TSP on resting platelets in the drawn blood sample.

Specifically, the Inventors have found that the physiological events which govern the presence of thrombospondin on the surface of resting platelets is exponentially increased by the excretion of thrombospondin by a small percentage of early "activated" circulating platelets. Relatively small numbers of circulating activated platelets are present during the early stages of platelet activation preceding a thrombogenic event. These undetectably low concentrations of activated platelets early in thrombosis posed a significant technical difficulty to others skilled in the art monitoring platelet activation through markers present on already activated platelets.[17, 33, 34, 36, 47, 42, 5, 48, 4, 49, 50, 8, 59, 6, 64, 24, 60, 61, 62, 63, 65, 66]

The interaction of TSP released from a small percentage of activated platelets, present for example in a nascent thrombus, with the entire circulating population of platelets (i.e., resting platelets), leads to an amplification phenomena with resting platelets which permits successful early platelet activation detection. Using the described unique "amplification" phenomena which occurs between thrombospondin released from a small number of activated platelets and the large population of resting platelets, the actual percentage of circulating activated platelets becomes irrelevant. For example, Applicant have found that a multiple-fold increase in the measurable amount of TSP results when resting platelets instead of activated platelets, are the cell population focused upon. This multi-fold increase of measurable thrombospondin occurs when the TSP released from activated platelets (in the early stages of platelet activation) interacts with surface TSP receptors on resting platelets. Any increase in resting platelet-associated thrombospondin is then monitored according to the methods of the present invention and used to predict a thrombotic event.

Limited platelet activation, a process which eventually leads to thrombus formation, is known to precede myocardial infarction, thrombotic stroke, and deep venous thrombosis.[17, 33, 34, 36, 47, 42, 5, 48, 4] Thus, the disclosed method for monitoring resting platelets as a signal of early platelet activation is expected to be therapeutically valuable in the prediagnosis and prevention of thrombotic events.

The detection of thrombospondin on the high affinity resting platelet thrombospondin surface receptors (rather than directly detecting activated platelets) is a novel approach which successfully overcomes the prior technical difficulties associated with predicting the onset of thrombosis and the difficulties of monitoring physiological changes in the small population of activated platelets during early thrombus formation. An important aspect of the present invention is to provide a thrombosis prediagnostic method which is capable of indicating the early onset of platelet activation through the monitoring of resting platelet physiological events which precede exponential platelet activation. A thrombotic event may thus be prediagnosed in sufficient time to avert or lessen the severity of its occurrence.

The unique amplification phenomena upon which the described methods and kits are predicted has not before been linked to a pre-indication of early thrombus formation. This concept is supported by the observation knowledge that high resting platelet thrombospondin levels (on the surface receptors of resting platelets) exist where increased numbers of activated platelets are found. Early thrombus formation has also been observed where there are high levels of activated platelets in the circulation. From these isolated observations, particularly claimed methods have been fashioned by which a thrombotic event may be prediagnosed.

The most preferred embodiments of the claimed diagnostic kit and methods include an anti-thrombospondin antibody which is capable of indicating the release of thrombospondin from a small percentage of early-activated platelets via immunoreactively detecting the released thrombospondins' interaction with the larger population of circulating resting platelets. The anti-thrombospondin antibody of the claimed invention may be either a polyclonal or monoclonal antibody.

Any artificial increase in the percentage of activated platelets in a patient sample can be avoided by proper handling techniques, which would include the drawing of the sample in the presence of acid citrate dextrose, PGEI (prostaglandin EI,) and theophylline.[7]

Any antibody having sufficiently high binding affinity for thrombospondin on resting platelets is expected to be useful in the claimed methods. More particularly, commercial preparations of thrombospondin may be used in preparing a detection reagent to detect thrombospondin expressed on resting platelet surfaces following the protocol described herein. Most preferably, the antibody of choice for use in the presently claimed methods is a monoclonal antibody. This monoclonal antibody is even more particularly F19D-2 monoclonal antibody. This particular monoclonal antibody has specific binding affinity for platelet-isolated thrombospondin present on the TSP surface receptors of platelets.

This particular antibody is produced by a hybridoma which has been deposited with the ATCC (HB#10516). Special utility of this antibody in the detection of TSP on the surface of resting platelets is indicted by preliminary results collected by the inventors. The anti-TSP antibody produced according to the methods described is indicated in these studies to have higher or greater binding affinity for TSP present on the surface of resting platelet surface TSP receptors as compared to TSP present on the surface of activated platelets. However, any hybridoma cell line prepared according to the methods provided herein with proper screening would be expected to produce monoclonal antibodies having binding affinity for thrombospondin present on resting platelets.

A most preferred method of obtaining and isolating thrombospondin from platelets in vitro is described by Lawler et al (1978).[26] The Lawler et al reference is specifically incorporated herein by reference for the purpose of providing one example by which thrombospondin may be isolated from platelets in vitro. However, other methods well known to those of skill in the art may equally efficacious..

One particularly preferred anti-thrombospondin monoclonal antibody is produced by a mouse hybridoma F19D-2, which is available in Inventors' laboratory at the University of Texas Health Science Center at Tyler, Texas at the following address:

The University of Texas Health Center at Tyler
Department of Biochemistry
P.O. Box 2003
Tyler, Texas 75710

Particular hybridoma cell lines which produce the described monoclonal antibodies, or monoclonal antibodies having identifying characteristics consistent therewith, are kept in the Inventors' laboratory. However, any hybridoma prepared according to the procedures particularly defined and disclosed herein, using the screening procedures described in the present application, may be expected to produce a monoclonal antibody having binding affinity for thrombospondin on resting platelets.

A most preferred mouse hybridoma which produces the described monoclonal antibody having binding affinity for thrombospondin present on platelet TSP receptors has been deposited with the ATCC (ATCC Accession No. HB 10516). The hybridoma cell line that produces the described monoclonal antibodies is deposited with the American Type Culture Collection facility located at the following address:

The American Type Culture Collection
12301 Parklawn Drive
Rockville, Maryland 20852

The referenced deposited hybridoma cell line has been deposited in accordance with the Budapest Treaty.

Methods of preparing the particular monoclonal antibody and the hybridoma which produces said monoclonal antibody directed against thrombospondin present on resting platelet TSP receptors are also included as part of the present disclosure. The inventors have found through comparative binding studies that the binding of the presently disclosed antibodies is specific for TSP, and preliminary studies indicate that the antibodies may further be specific for only that TSP present on the surface of resting platelet surface TSP receptors. The antibody employed in the present studies (F19D2) is provided to satisfy all best mode requirements. Other monoclonals such as TSP1-1 may also be used.[7] (See FIG. 6 —TSP-1 vs. F19D2).

Another particularly advantageous feature of the described diagnostic methods is that it provides a relatively inexpensive method by which a clinician may effectively intervene to halt platelet activation before or early in the thrombotic disease process. In a most preferred embodiment of the invention, a method of identifying a patient at risk of a thrombotic event is described which comprises obtaining a blood sample from the patient; isolating the platelet fraction comprising resting platelets from the blood sample; determining the amount of thrombospondin on the resting platelets; and identifying those blood samples having an elevated amount of thrombospondin on resting platelets, wherein a patient-sample identified as having an elevated level of thrombospondin on resting platelets indicates a patient at risk of a thrombotic event. In this method, a patient with an elevated level of thrombospondin, most specifically thrombospondin present on resting platelet TSP surface receptors, is predicted to be at risk of a thrombotic event, most specifically when the number of resting platelet-associated thrombospondin molecules is greater than an established normal range. Alternatively, a number of resting platelet associated thrombospondin molecules of at least 200 molecules or most preferably at least 250 molecules of thrombospondin per resting platelet is an elevated level.

Once an elevated thrombospondin concentration or level is determined to exist on the surface of the population of resting platelets in a blood sample, then any anti-thrombotic medication may be used in methods well known to those of skill in the art for achieving an anti-thrombotic physiological condition in the patient, that is, effective to "inactivate" the platelet population. These agents render platelets less susceptible to activation and aggregation, thereby protecting the patient from future thrombotic events.

The present invention also comprises a method by which post-thrombosis patients may be monitored to determine whether a particular "anti-thrombotic" pharmaceutical agent or treatment regimen is acting to return the patient's circulating platelets to a non-threatening, "inactivated" platelet level. Such would be accomplished through monitoring the extent of TSP platelet surface expression at frequent intervals after the pharmaceutical agent has been administered. An attending physician would then be able to modify or change the treatment regimen of a patient whose resting blood platelet population does not demonstrate a decrease in the percent of platelets expressing TSP.

The present invention provides a method for preventing a thrombotic event in a patient comprising: identifying a patient having elevated resting platelet thrombospondin levels; and administering to the identified patient a pharmacologically acceptable antithrombotic pharmaceutical agent.

While any of a number of anti-thrombogenic pharmaceutical agents known to those of skill in the art may be used to halt ongoing platelet activation and thrombus formation, particular examples of such agents are heparin and acetylsalicylic acid (i.e. aspirin) or other antiplatelet agent effective in preventing platelet activation in vivo.

A particularly preferred method for identifying a patient having an elevated thrombospondin level comprises: obtaining a blood sample from the patient to form a test sample comprising resting platelets; mixing a known quantity of the test sample with a known quantity of an antibody capable of binding thrombospondin on resting platelets to form a test mixture; maintaining the test mixture for a time period sufficient to allow the antibody to bind thrombospondin present on the resting platelet thrombospondin receptors to form a complexed antibody; separating the complexed antibody complexes from the test mixture; determining the level of thrombospondin on the resting platelets in the blood sample from the amount of complexed antibody present in the test mixture, (and thereby the level of thrombospondin on the resting platelets in the blood sample); and identifying a patient having an elevated level of thrombospondin on resting platelets as a level greater than about 200 molecules of thrombospondin per resting platelet, wherein an elevated level of thrombospondin identifies a patient at risk of a thrombotic event. Alternatively, an elevated level of thrombospondin may be indicated as a level of resting platelet thrombospondin above an established normal resting platelet thrombospondin range.

In a most particularly preferred embodiment of the described methods, the patient is a human. Thus, a particularly preferred biological blood sample to be analyzed with the described methods and diagnostic kit is a human blood sample comprising human resting blood platelets.

In that the present invention also comprises particularly defined diagnostic kits for prediagnosing persons at risk of a thrombotic event, or for measuring thrombospondin levels in a biological sample in general, a preferred embodiment of the kit may be described as comprising: a carrier means adapted to receive at least three container means in close confinement therewith; a first container means comprising an anti-thrombospondin antibody (labeled or unlabeled) capable of selectively binding thrombospondin on resting platelets, most particularly, that thrombospondin on human resting platelet surface thrombospondin receptors; a second container means comprising an antibody detection reagent; and a third container means comprising a specificity control reagent, such as thrombospondin isolated from a preparation of platelets.

In a most preferred embodiment of the diagnostic kits, an anti-thrombospondin antibody is used to immunologically detect thrombospondin on the surface of resting platelets in a biological sample, for example, an $I^{125}$-labeled anti-thrombospondin antibody. Even more preferably, the anti-thrombospondin antibody is a monoclonal antibody produced by mouse hybridoma ATCC # HB10516.

The methods and diagnostic kits of the present invention function to monitor a pre-thrombosis resting platelet phenomena through the use of an antibody "tag" specific for thrombospondin. This antibody "tag" has a specific and strong binding affinity for thrombospondin present on resting platelet surface TSP receptors. The particular antibody of the disclosed methods and kits features the ability to bind thrombospondin present on those TSP receptors of resting platelets.

The diagnostic kit of the present invention in a most particularly preferred embodiment comprises a fluorescent bead system, and is constructed of a durable and lightweight plastic material.

The blood sample with resting platelets to be analyzed most preferably should be analyzed as soon as possible after having been drawn, but may also be analyzed subsequent to drawing up to 7 days. Such samples should be paraformaldahyde fixed before storage until assay.

The various container means to be included with particular embodiments of the kit most preferably are constructed of a non-pyrogenic biocompatible material which is impact resistant, and should be sealed sufficiently so as to prevent contaminants from infecting the purity of the substances included in the container means.

Most preferably, the first container means of the claimed diagnostic kit comprises an unlabeled antibody capable of binding with thrombospondin on resting platelets. Most particularly, the antibody is a monoclonal antibody. Even more preferably, the monoclonal antibody is produced by Inventors' deposited mouse hybridoma F19D-2 (ATCC # HB 10516).

The kit may also optionally include a container means comprising a blood anticoagulant to receive the biological test sample and a container means comprising a 20% solution of sucrose. Most preferably, the detecting reagent comprises fluorescent carboxylate microbeads (Polysciences, Warrington, PA) with IgG binding affinity.

An alternative method for quantifying resting platelet thrombospondin is based on cell counts following incubation of a sample with an antibody to TSP and magnetized beads coated with either anti-mouse IgG or anti-rabbit IgG (Magnasort, New England Nuclear, Boston, MA) (depending on whether the primary antibody is a polyclonal or a monoclonal antibody).

Additional methods include the use of a radiolabeled antibody in cell-ligand binding assays,[7] a fluorescent anti-TSP antibody for flow cytometry, or an unlabeled anti-TSP antibody detected with a radiolabeled or fluorochrome labeled second antibody in either ligand binding assays or flow cytometric analysis may be used in conjunction with the described antibody capable of binding to thrombospondin, preferred labels, by way of example, include a radioisotopic label, a fluorescein label, or an enzyme label.

The present invention is described using terms which express the relative states of the subject platelet populations being monitored. The terms "non-stimulated platelet" and "resting platelet" are used interchangeably herein to denote a normal, free flowing blood platelet that has not been exposed to a physiological stimulus. Conversely, the terms "stimulated" platelet and "activated" platelet are used interchangeably herein to denote a blood platelet that has been exposed to a physiological stimulus either in vivo or in vitro, and which is therefore, in an active state. Activated platelets typically express a variety of proteins, including fibronectin, fibrinogen, von Willebrand factor and thrombospondin. One example of a physiological agent which will stimulate and transform resting platelets to activated platelets is thrombin.

To avoid limitations associated with methods which depend upon the concentration of activated platelets, and to attain a more effective predictive patient evaluation, an object of the present invention is the development of a diagnostic test which is not dependent on high concentrations of circulating activated platelets. The disclosed diagnostic system for predicting a thrombotic event is possible in a patient having less than an about 0.8% total stimulated circulating platelet level, even to levels of about 0.2% total stimulated circulating platelet levels. The presently proposed system is independent of activated platelet levels, render consistent results specific for those physiological events preceding thrombosis, and would be a relatively easy clinical measurement to perform.

The terms magnetobead, magnetic beads and magnetic microbeads are used interchangeably in the specification. The platelet protein, thrombospondin, useful as an antigen in the present invention is normally present on the outer cell surface membrane of resting platelets in very small amounts.

The following abbreviations are used throughout the Specification:
TSP=thrombospondin
Fg=fibrinogen
Fn=fibronectin
vWF=von Willebrand factor
Kd=dissociation constant
M=nanomolar
βTG=Beta-thromboglobulin
Ca=calcium ion
Mg=magnesium ion
ADP=adenosinediphosphate
EDTA=ethylenediamine tetraethylacetate
PPACK=D-phenylalanyl-L-prolyl-L-arginine-chloromethylketone
μg=microgram
μl=microliter
PGEI=prostaglandin E1
ACD=acid citrate dextrose
BSA=bovine serum albumin
IgG=immunoglobulin G
ml=milliliter

Lane 1—$^{125}$I-TSP and 2mM Ca.

Lane 2—$^{125}$I-TSp bound to resting cells.

Lane 3—$^{125}$I-TSP bound to thrombin stimulated cells.

Lane 4—Plasmin digest of $^{125}$I-TSP and 2mM Ca.

Lane 5—Plasmin digest components bound to resting cells.

Lane 6—Plasmin digest components bound to stimulated cells.

Lane 5 provides additional evidence that the TSP receptor on resting platelets is a high affinity TSP binding site. The resting cells bound only intact TSP which was a minor component of the digest (not even discernable in lane 4 of the gel).

Figure 3B:
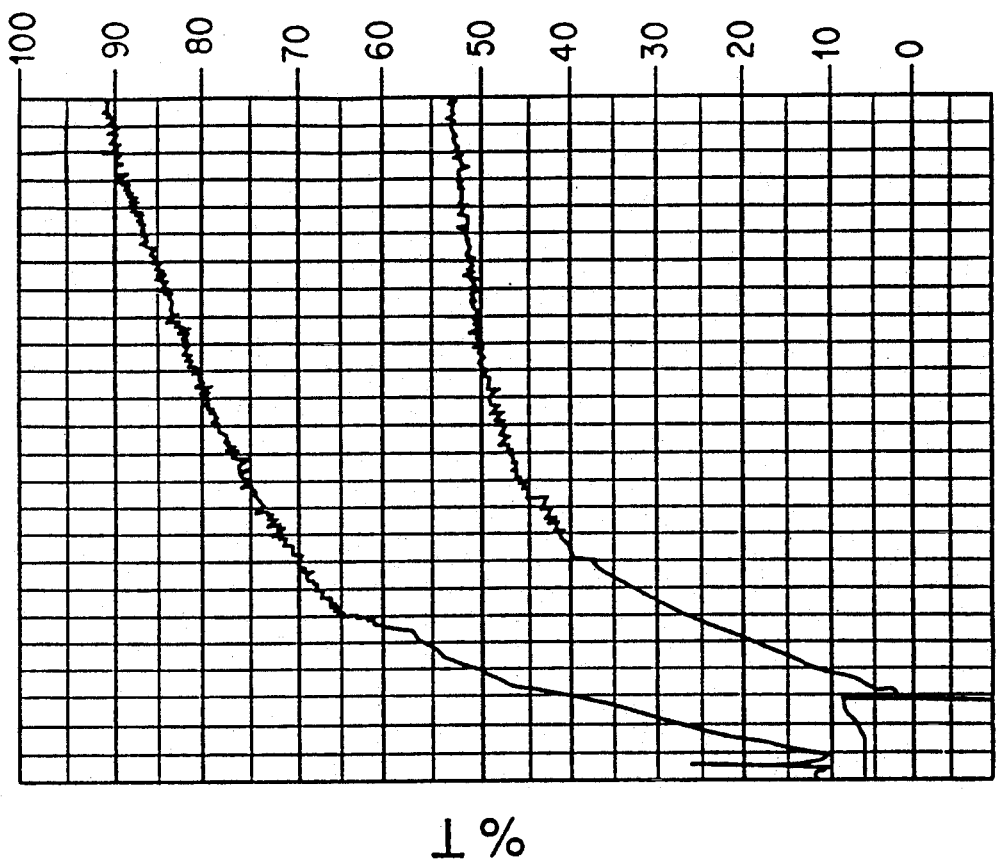
Figure 3A:
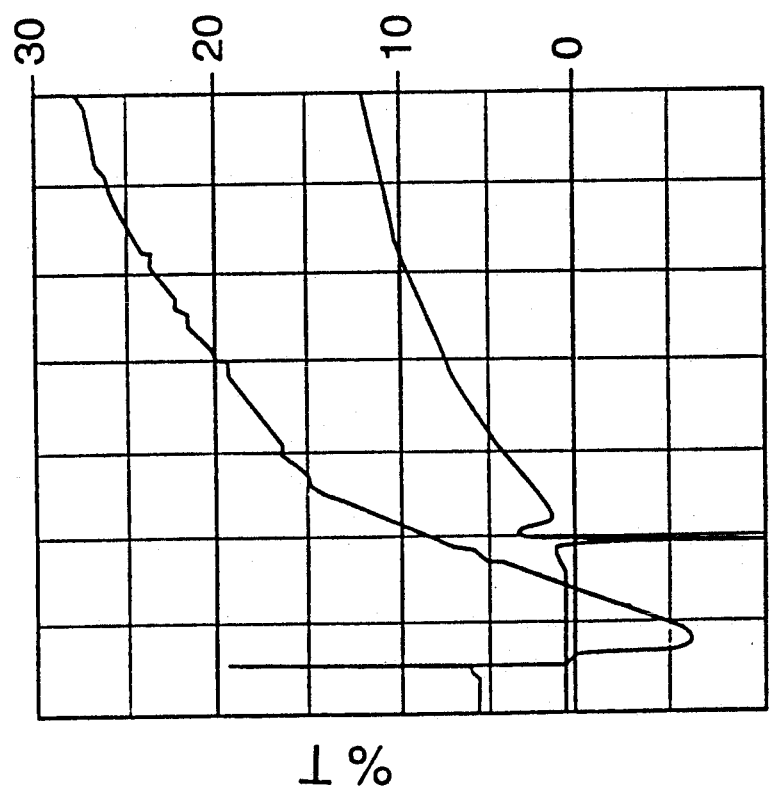

FIG. 3—Inhibition of Platelet Aggregation by TSP. Washed human platelets at a final concentration of 1×$10^8$/ml were incubated in an aggregometer with stirring at 37° C. with TSP at a final concentration of 380 nM prior to stimulation with 10 μM ADP. The arrow indicates the point at which ADP was added. The percent transmittance of light (%T) is plotted vs. time. Left Panel (FIG. 3A)—No exogenous Fg added Right Panel (FIG. 3B)—Exogenous Fg present at a final concentration of 300 nm. In both experiments the lower line represents platelets preincubated with TSP, while the cells exhibiting the more extensive aggregations response were not incubated with TSP. This experiment indicates that resting platelets with TSP on their surface are less responsive to platelet agonists. This phenomena may serve to protect from exponential platelet activation early in thrombotic disease, thus TSP coated resting cells will be present for a period of time prior to a thrombotic event. This is an important phase when detection of TSP on resting cells can be measured and therapy started prior to a thrombotic event.

Figure 4:
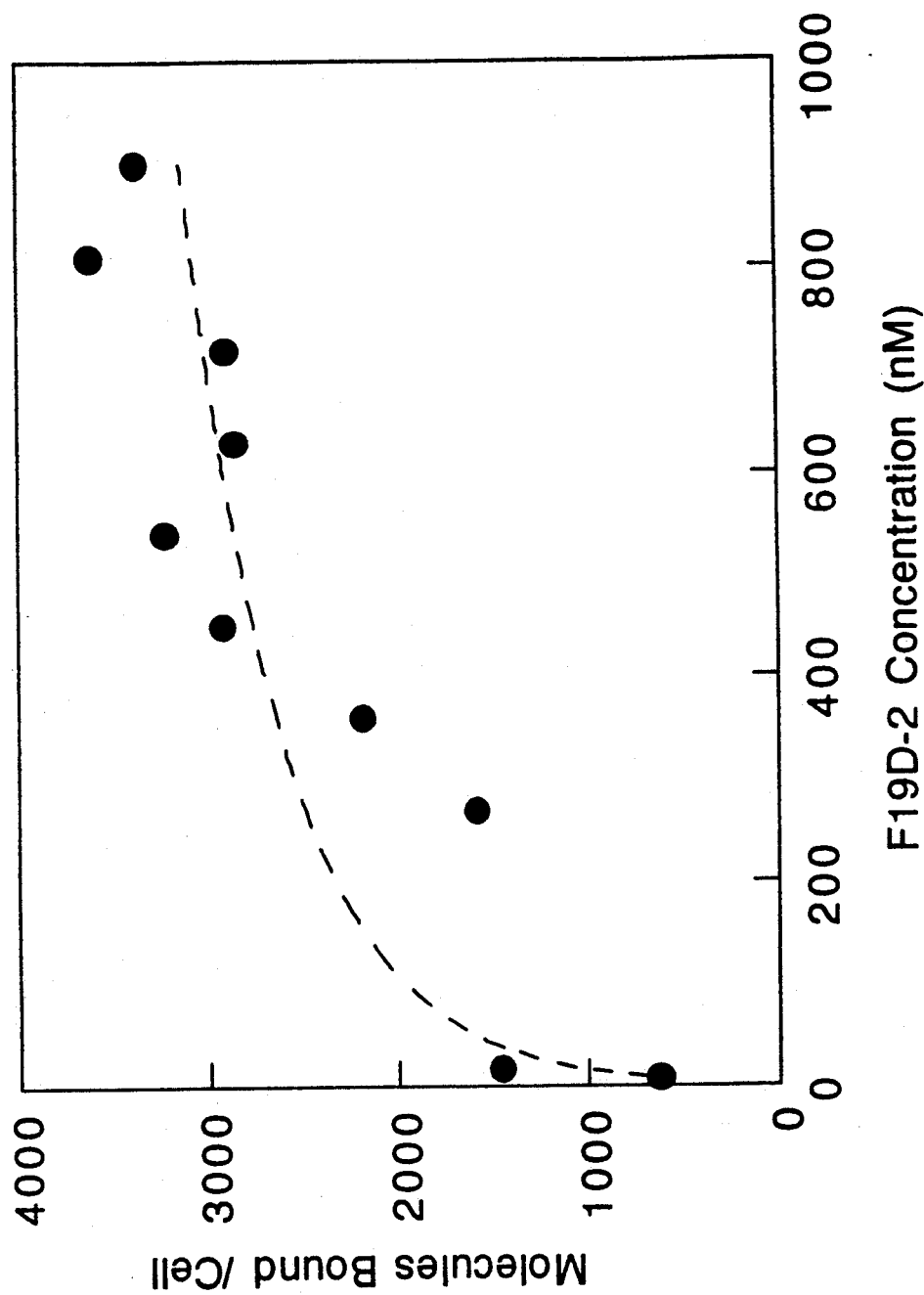

FIG. 4 —F19D-2 binding to paraformaldehyde fixed platelets in the presence of 5mM EDTA. The graph demonstrates that a plateau of between 3,000–3,500 molecules of thrombospondin per platelet is reached in the presence of about 500 nM of the F19D-2 anti-thrombospondin antibody. This level of binding is characteristic of the cation-independent, high affinity receptor.

Figure 5:
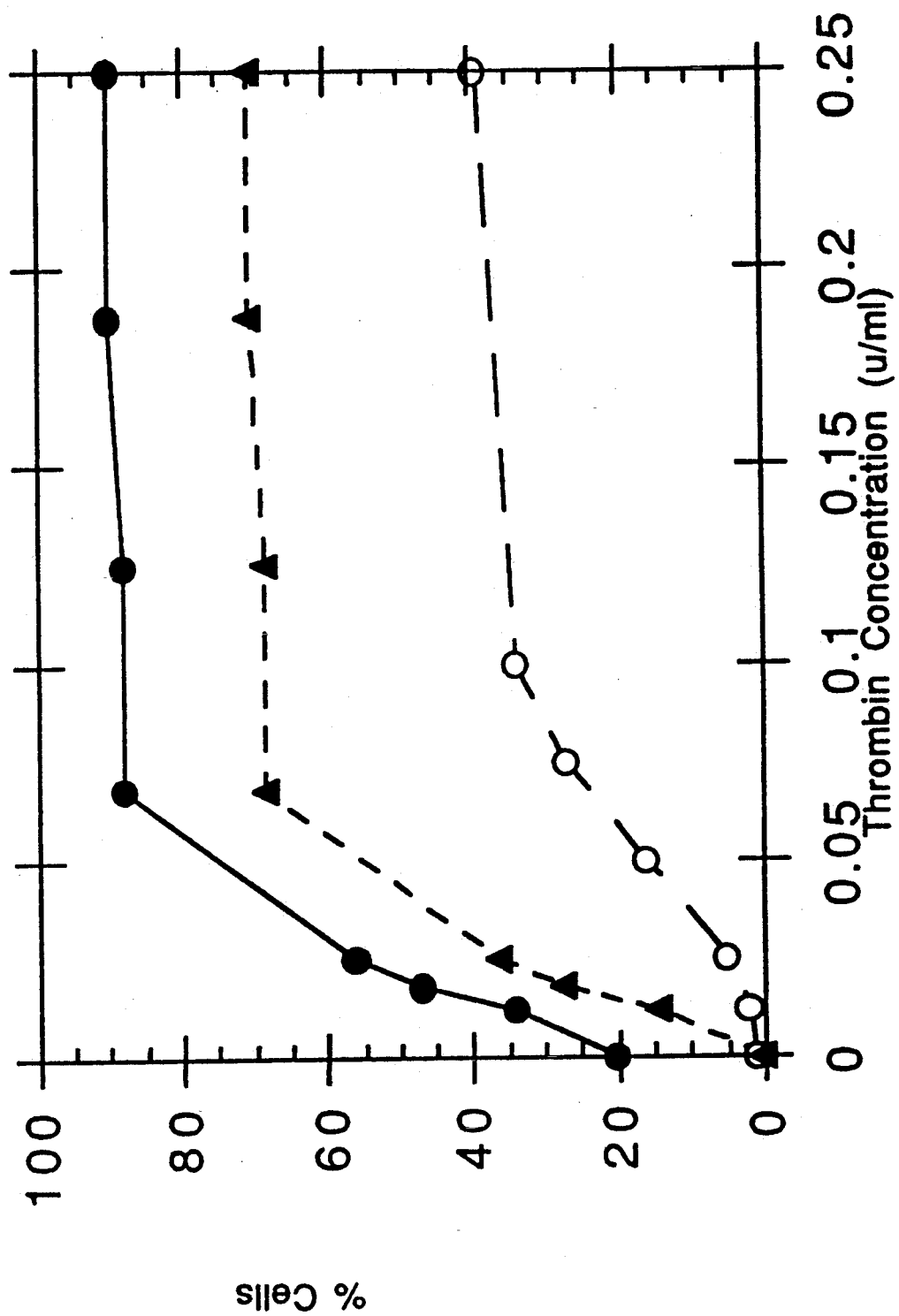

FIG. 5—TSP and GMP-140. Total cells pelletted (●) is plotted against cells specifically pelleted as determined the binding of TSP-positive cells to Magnasort immunobeads (New England Nuclear, Boston, MA (▲), and cells positive for with GMP-140 (○) as published by George et al.[82] The latter measurements were performed by flow cytometric analysis using a fluorescein conjugated monoclonal antibody specific for GMP-140. Measurement of TSP surface expression by the magnetic bead assay is more sensitive in measuring platelet activation than GMP-140 surface expression (which only occurs on activated cells). As measured by George et al., note that a majority of the cell population exhibits surface-bound TSP under conditions where little activation is noted by GMP-140 expression. This indicates that TSP is bound to the majority population of resting platelets rather than an activated population of cells.

Figure 6:
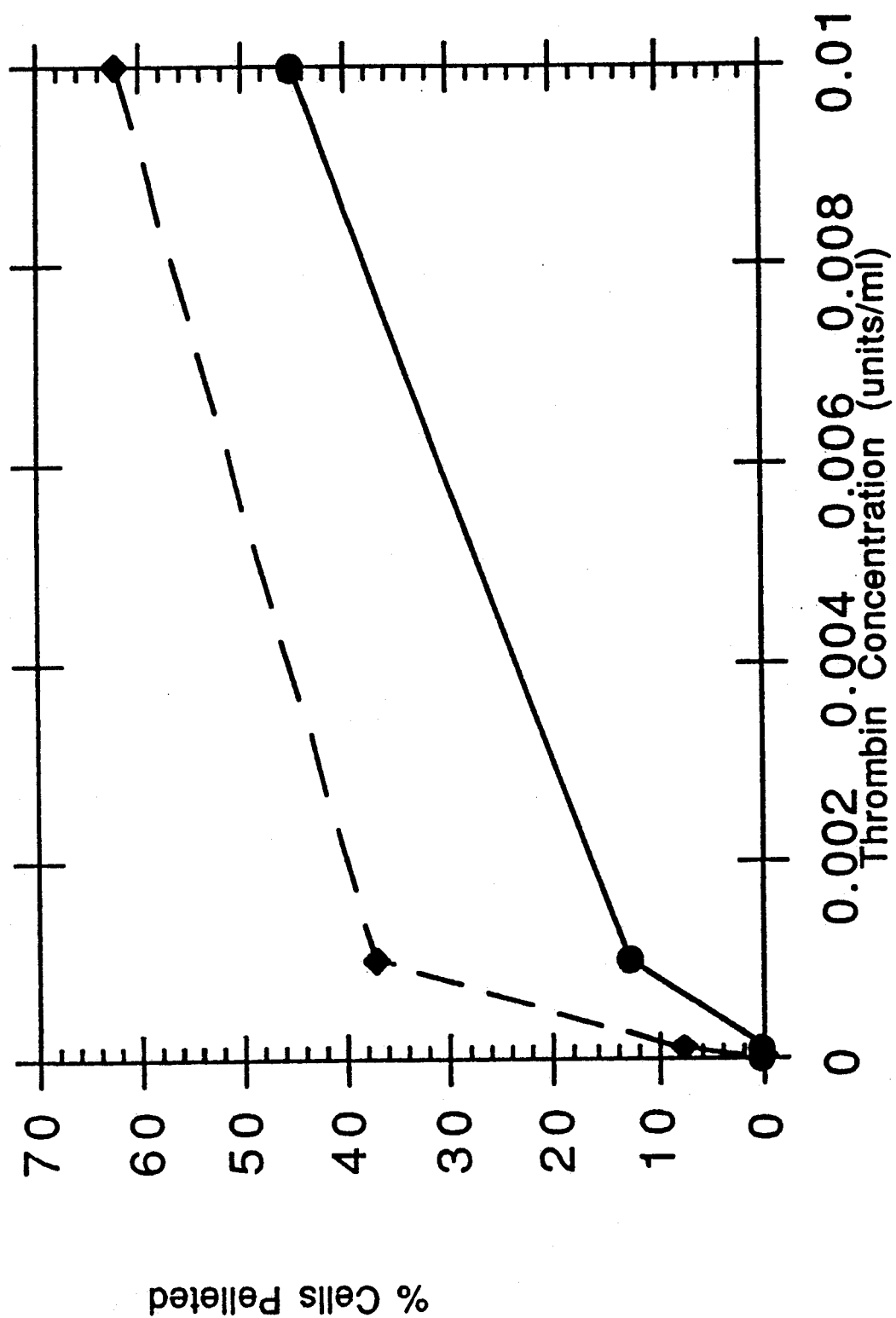

FIG. 6—TSP1—1 compared to F19D-2 —The two antibodies were compared in the magnetic bead assay for TSP surface expression. Both antibodies were effective. (♦—TSPI-1; ●—F19D-2)

Figure 7:
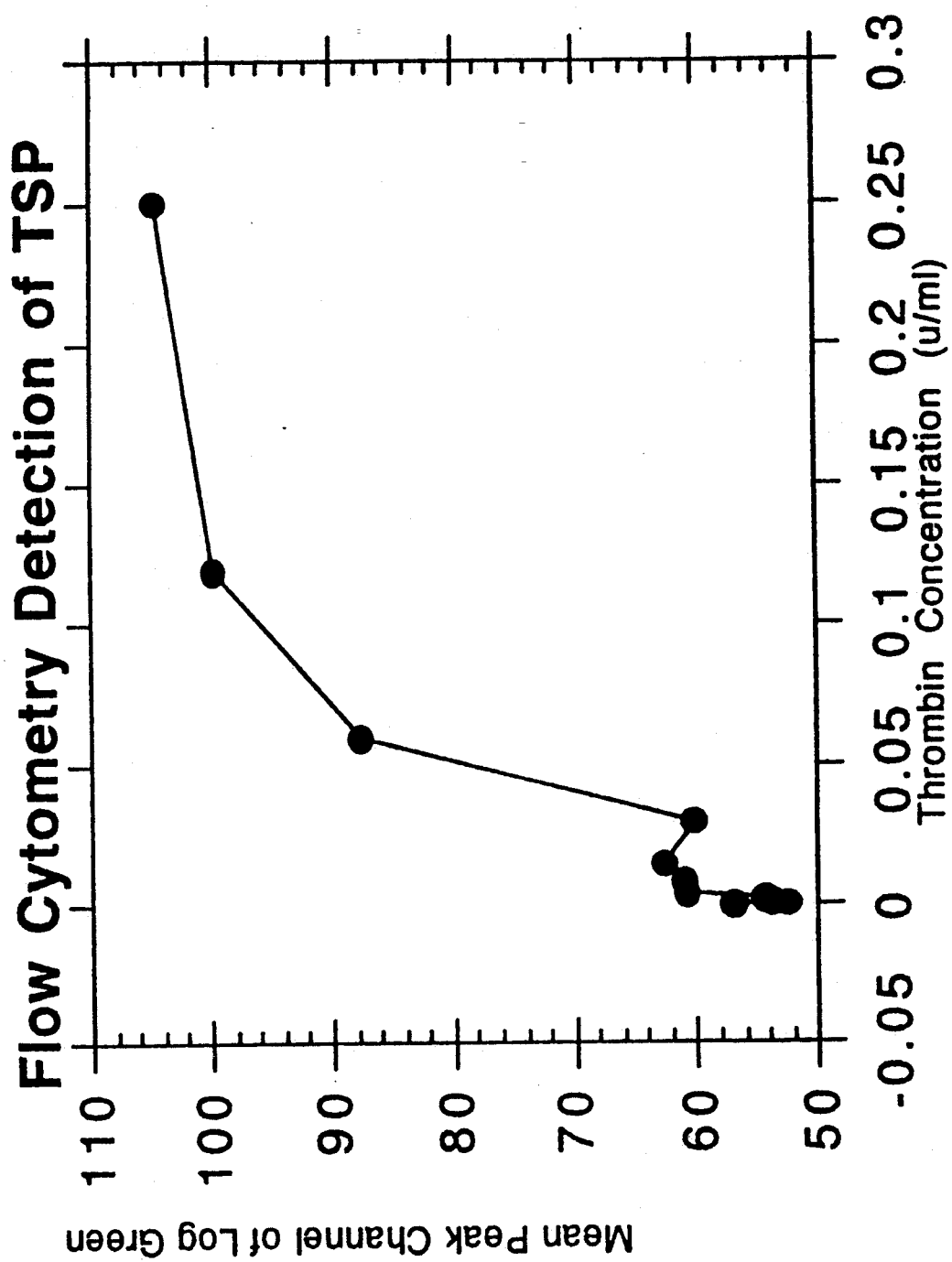

FIG. 7—Flow Cytometry Detection of TSP. The graph demonstrates an increase in the mean peak channel of log green with increasing concentrations of thrombin. Platelets were incubated with the indicated concentrations of thrombin, fixed with paraformaldehyde, and stained with rabbit polyclonal anti-TSP Fab fragment as described in Examples 3 and 7. The washed cells were counterstained with a fluorescein labeled goat anti-rabbit IgG antibody, washed by centrifugation and analyzed by flow cytometry. The data represent the mean peak of fluorescent intensity and are directly correlated with the number of bound TSP molecules per platelet.

Figure 8:
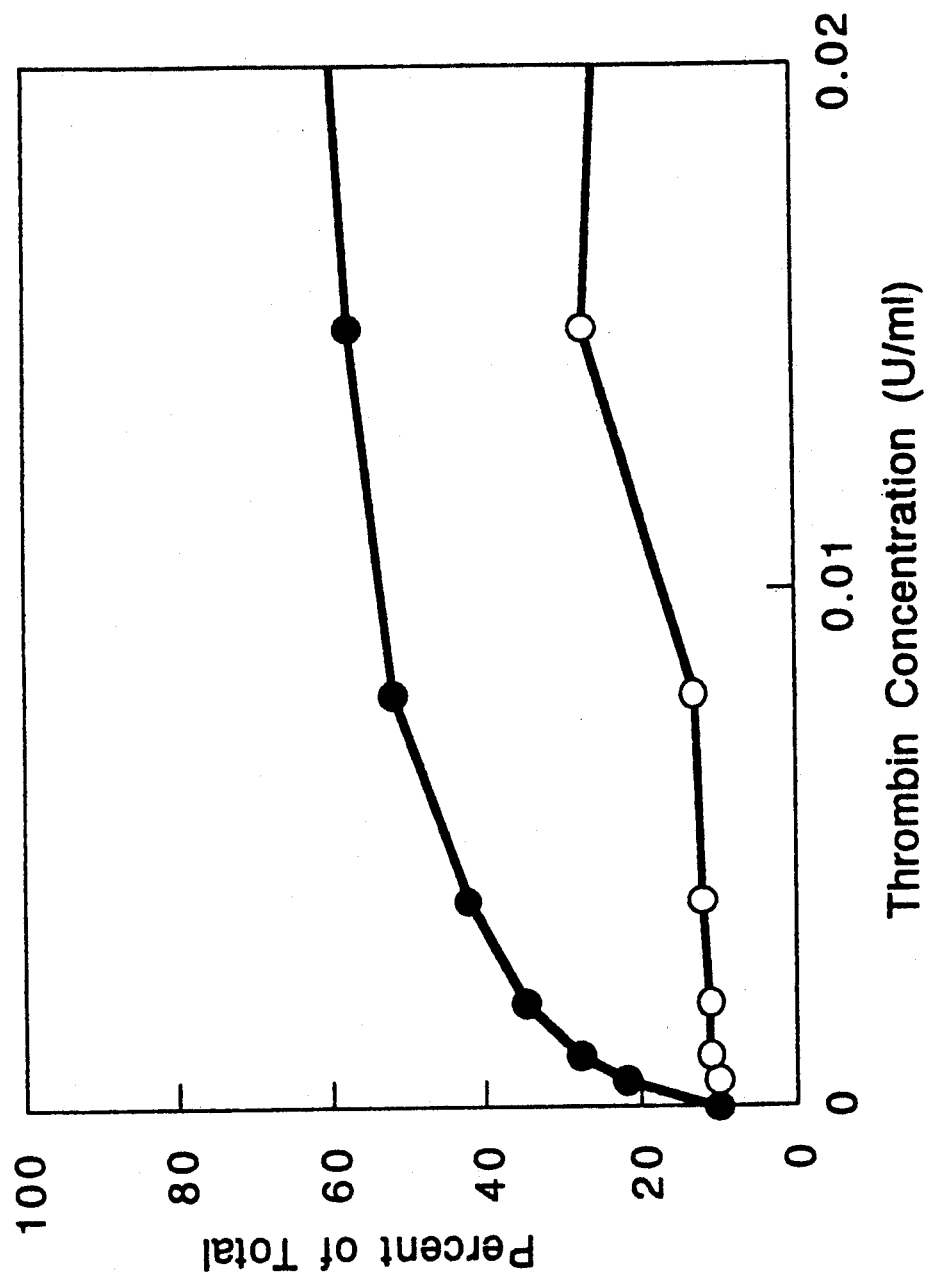

FIG. 8—Increase in the percentage of surface TSP positive cells as determined in FIG. 7 (-⬧-) against the increase in percent βTG secretion by activated platelets in the sample as a function of increasing concentrations of thrombin (Units/ml) (●—TSP; O—βTG). Note the much higher sensitivity of the surface TSP assay as compared to the βTG assay.

Figure 9:
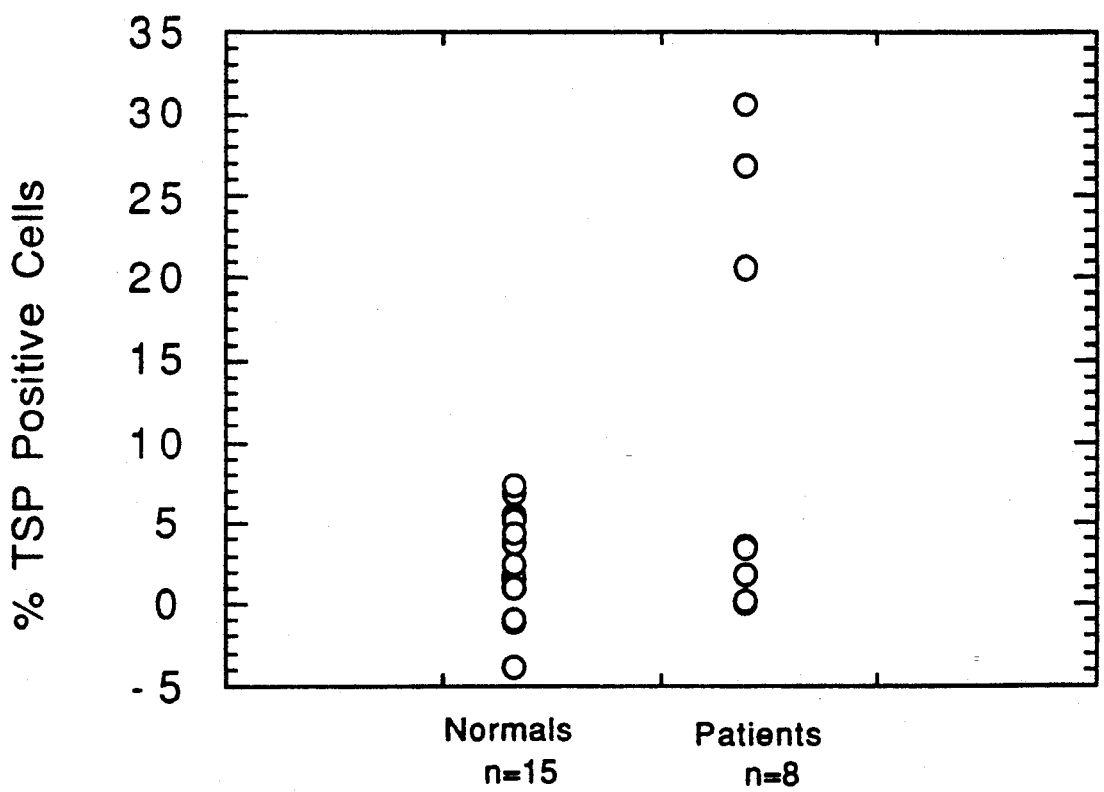

FIG. 9—Surface TSP levels on Platelets from Normal Individuals and Cardiovascular Patient Blood Samples. The percentage of platelets binding one or more fluorescent microbeads was determined by the enhanced flow cytometric method described in Example 9. Note that 3 patients show levels that are significantly higher than the normal population ($p < 0.0001$)

Figure 10:
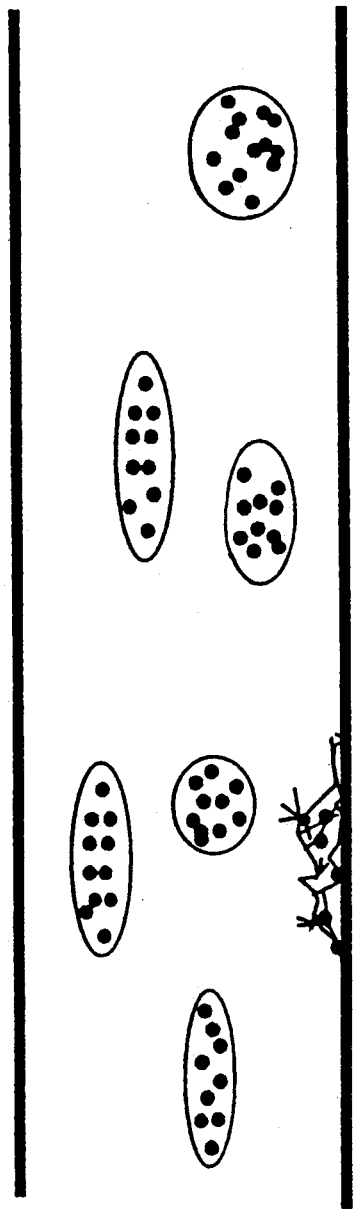

FIG. 10—Schematic Representation of "Amplified" Signal for Detection of Platelet Activation.

DETAILED DESCRIPTION OF THE PREFERRED EMBODIMENTS

The present invention relates to the previously unconsidered diagnostic utility of monitoring proteins associated with resting platelets as a method for predicting a thrombotic event in a patient. More specifically, the surface concentration of TSP on resting platelets is described as a method which provides an early physiological indicator of thrombus formation.

In its most basic embodiment, the present invention discloses a method for predicting a thrombotic event or detecting a prethrombotic event in a patient through monitoring resting platelets. This method more specifically relies on the detection of thrombospondin on a resting platelet surface. A particularly preferred embodiment of the described method comprises exposing a biological sample having resting platelets possibly having surface-associated thrombospondin to an antibody capable of binding thrombospondin present on resting platelets (i.e., an anti-thrombospondin antibody). More specifically, the anti-TSP antibody of the described methods binds to thrombospondin which is associated with the platelet surface at thrombospondin resting surface receptors.

Resting TSP platelet surface receptors comprise a distinct population of platelet surface receptors from those thrombospondin (TSP) receptors which exist on the surface of activated platelets. These two populations of platelet TSP surface receptors have different binding affinities for thrombospondin.[5]

In a particularly preferred embodiment of this method, the antibody is either a monoclonal antibody or a polyclonal antibody. The antibody most preferably is a monoclonal antibody. The particular monoclonal antibody having binding affinity for thrombospondin on resting platelets, F19D-2 is available in the Inventors' laboratory. Also, the particular hybridoma which produces the described monoclonal antibody F19D-2 has been deposited with the ATCC (ATCC # HB 10516). This deposit has been made in order to even more fully assure that the best mode of practicing the invention has been provided.

However, any anti-thrombospondin antibody having a specific and sufficiently high binding affinity for thrombospondin present on the surface of resting platelets may be used in conjunction with the described methods. A most preferred antibody is a monoclonal antibody that is produced by hybridoma ATCC #HB10516.

The antibody of the present invention is further characterized in that it specifically binds to thrombospondin bound to the cation-independent, high affinity TSP receptor on the surface of resting platelets.

One feature of the described diagnostic and prediagnostic methods is that it provides the opportunity to clinically abort continued platelet activation before the level of activated circulating platelets reaches detectable concentrations. At "detectable" activated platelet concentrations described for assay methods which monitor activated platelets directly, the ability to halt the continued platelet activation which precipitates thrombus formation becomes extremely limited, if not completely foreclosed. A particular object of the described methods is to prevent a thrombotic event through the prevention of the exponential and rapid increase in platelet activation once the activation of a very small percentage of platelets is detected.

According to the present invention, a prethrombotic state is identifiable even when the circulating concentration of activated platelets are below currently available "detection" levels, and is employed to effectively halt continued platelet activation and thrombus formation. The term, "prethrombotic state" as used in the present application is defined as that physiological state of a patient determined to have elevated levels of resting platelet-associated thrombospondin. An elevated level of thrombospondin is defined as a number of resting platelet-associated thrombospondin molecules greater than 30-225 molecules per resting platelet[7] or a percent of positive cells above established normal range.

A preferred embodiment of the method for prediagnosing a patient at risk of a thrombotic event comprises: obtaining a biological sample including resting platelets from the patient suspected to be at risk of a thrombotic event; determining the amount of thrombospondin on the resting platelets; and identifying those biological samples having an elevated amount of thrombospondin on resting platelets; wherein a patient sample identified as having an elevated amount of thrombospondin on resting platelets indicates a patient at risk of a thrombotic event.

Currently work is underway to develop a standard mean "normal" value of the number of molecules of thrombospondin per cell or a percentage of positive cells against which to determine elevated levels of thrombospondin. The Inventors have outlined a protocol herein whereby a mean-normal baseline of thrombospondin is to be developed through screening a representative number of samples obtained from healthy adults between the ages of 18-36 who have no known history of a thrombotic event. The average number of resting-platelet associated thrombospondin molecules or, alternatively, the percentage of TSP positive cells, will then be used as the baseline "mean" value against which test samples will be evaluated.

Preliminary experiments already obtained (FIG. 9) using 15 such individuals suggest that the normal range is approximately 2.71% +/−3.65 when measured by the fluorescent microbead assay.

Previous direct radiolabeled antibody assays have detected an average of 200 or less TSP molecules per resting platelet.[7] This figure represents about 5% of the total cation independent, high affinity sites available for binding. Thus, both methods yield normal estimates of about 3-5% of maximal binding for the normal mean value. These data indicate that the blood collection methods currently employed do not significantly contribute to artifactual platelet activation.

Thus, it is proposed that an elevated number of thrombospondin molecules on resting platelets for purposes of prediagnosis, comprises an average number of resting platelet-associated thrombospondin molecules greater than about 200 molecules thrombospondin per resting platelet, or about 3-5% of the maximal binding possible to the high affinity receptor.

The level of thrombospondin present on resting platelets may be determined using standard laboratory techniques for detecting and quantifying the presence of an antigen. However, the particularly preferred methods by which the present invention may be practiced include: flow cytometry, radioimmunoassay, and a magnetic bead assay. All of these methods employ an anti-thrombospondin antibody having binding affinity for thrombospondin present on the surface of resting platelets. The anti-thrombospondin antibody most preferably is a monoclonal antibody. Thus, such antibodies constitute a reagent included in the described most preferred detection methods (magnetic bead antigen detection assay, a flow cytometric assay (using a fluorescein-labeled anti-thrombospondin antibody, or unlabeled anti-thrombospondin polyclonal or monoclonal antibody followed by fluorescein labeled anti-mouse or anti-rabbit antibody or most preferably, fluorescent protein-A conjugated carboxylated microbeads), and a radiolabeled ligand binding assay. A detailed description of each of these particular assays adapted to detecting thrombospondin as antigen on resting platelets is presented in the examples which follow.

Regardless of the particular assay technique employed, the assay in a most preferred embodiment will include the anti-thrombospondin monoclonal antibody obtained from the ATCC deposited hybridoma cell line, HB 10516 or a polyclonal anti-thrombospondin antibody having binding affinity for thrombospondin species present on resting platelets.

A preferred embodiment of the proposed diagnostic method for prediagnosing a person at risk of a thrombotic event comprises detecting the presence of elevated levels of TSP on resting platelet TSP surface receptors, which method in turn initially comprises determining the thrombospondin level present on resting platelets with in a patient sample an anti-thrombospondin antibody capable of binding to thrombospondin present on resting platelets and an antibody detection reagent; and prediagnosing a patient at risk of a thrombotic event in a patient having a thrombospondin level greater than 200 molecules thrombospondin per resting platelet.

Determining the level of TSP, and therefrom, identifying a patient with elevated thrombospondin levels at risk of a thrombotic event, comprises: obtaining a blood sample from the patient to form a test sample comprising resting platelets; mixing a known quantity of the test sample with a known quantity of an anti-thrombospondin antibody capable of binding thrombospondin on resting platelets to form a test mixture; maintaining the test mixture for a time period sufficient to allow the antibody to bind thrombospondin on the resting platelets to form a antibody-platelet complex; separating the antibody-platelet complex from unbound antibody (preferably by centrifuging the cells through a 20% sucrose cushion); determining the amount of labeled antibody associated with the antibody-platelet complex in the test mixture; and converting this data to molecules of TSP per resting platelet, wherein a patient with elevated thrombospondin levels is identified as a patient having greater than 200 molecules of thrombospondin per resting platelet. Alternatively, an elevated thrombospondin level may be identified in a patient with a percentage of positive resting platelet cells with surface thrombospondin which exceeds an established normal range.

In assays for surface-bound thrombospondin, the amount or extent of antibody associated with the resting platelet cells separated from the test mixture is used to determine the level or extent of thrombospondin in the patient resting platelet blood test sample according to methods well known to those of skill in the art. A patient with an elevated level of resting platelet thrombospondin is predicted to be at risk of a thrombotic event.

In a particularly preferred embodiment of the described method for identifying a patient at risk of a thrombotic event, the method by which thrombospondin is determined in a sample is further described as most preferably including an incubation step wherein the test mixture is maintained for between about 30 minutes and about 90 minutes at about 22° C. or 37° C.

The anti-thrombospondin antibody of the described methods and kits may be either a monoclonal antibody or a polyclonal antibody. In a more preferred embodiment of the described methods and kits, the antibody is a monoclonal antibody, and even more particularly is the monoclonal antibody, F19D-2, produced by an ATCC deposited hybridoma cell line, HB 10516.

The monoclonal antibody most preferably may be labeled with an enzyme, a fluor, a radioisotope, or even more preferably detected by an indirect method. Most preferably, the monoclonal antibody is indirectly detected with a immunoglobulin detection reagent. The detection reagent in an especially preferred embodiment of the described method are fluorescent carboxylated microspheres coated with an agent which specifically binds to the anti-TSP antibody. Such agents may include protein A, anti-mouse IgG, or protein G. The most preferred fluor is fluorescein.

Alternatively, the fluor may be Texas Red, phycoerythrin or rhodamine or its derivatives. Alternatively, the monoclonal or polyclonal antibody or an antibody specific for mouse or rabbit IgG may be labeled directly with a fluor, for example, with the fluorochrome Texas Red, fluorocein, phycoerythrin or rhodamine.

Using the described labeled antibodies, thrombospondin-laden resting platelets may be detected using a flow cytometer which measures relative fluorescent intensity of individual cells within the platelet population. By using a reference standard or comparing to the radiolabeled ligand binding data, the fluorescence can be accurately quantitated and the number of TSP molecules per cell calculated.

As used in the present application, an elevated level of thrombospondin on resting platelet surface receptors is generally defined as the presence of more than 200 molecules, most preferably 225 molecules, of thrombospondin per resting platelet.[7] Preliminary data using platelets prepared as outlined in Example 4 and measured as described in Example 10 suggest that a level of 2.91% +/−3.65 of positive platelets represents a reasonable estimate of the normal mean (N=15). An elevated thrombospondin level is to be determined as against a resting platelet thrombospondin base line level established from a representative number of autonomous, prethrombotic patient samples measured for resting platelet-associated thrombospondin.

Among the possible future thrombotic events believed to be indicated by elevated TSP levels on resting platelet surfaces in human patients are thrombosis, stroke, deep venous thrombosis, pulmonary embolism, cardiovascular disease and myocardial infarction.

One preferred application of the present invention lies in the prevention of a thrombotic event in a patient determined to be at risk of such events. In a particularly preferred embodiment of the described method for preventing a thrombotic event in a patient at risk, the method comprises the steps of identifying a patient having elevated thrombospondin levels, and administering to the identified patient an antithrombotic pharmaceutical agent. In a preferred embodiment, the antithrombotic pharmaceutical agent to be administered to a patient identified at risk of a thrombotic event is heparin, acetylsalicylic acid, or other such agents that prevent platelet activation.

In the above described method of preventing a thrombotic event, the step of identifying a patient having elevated thrombospondin levels comprises: obtaining a patient blood sample comprising resting platelets; and determining the amount of thrombospondin present on the resting platelets in the patient blood sample. The level of thrombospondin present in the patient blood sample of resting platelets is then compared to a mean resting platelet thrombospondin level.

Even more specifically, determining the amount of thrombospondin present in a patient sample comprises the steps of: preparing a platelet-rich plasma sample (preferably by centrifuging a patient blood sample) to provide a (supernatant of a) platelet-rich plasma sample comprising resting platelets (the plasma supernatant being essentially erythrocyte and leukocyte free); exposing a known amount of the platelet-rich plasma sample to a known amount of an antibody capable of binding thrombospondin on resting platelets to form a test mixture tube; preparing a second tube comprising a known amount of patient platelet-rich plasma and exposing the second tube to a known amount of an antibody rendered incapable of binding platelet surface thrombospondin on resting platelets to form a negative control tube; incubating both the test mixture tube and the negative control tube a period of time sufficient to allow binding of thrombospondin present in the test mixture tube and the negative control tube to the antibody to form complexed antibody; to form complexed antibody; exposing the complexed antibody in the test mixture tube and the negative control mixture tube to a sufficient quantity of an antibody detection reagent capable of binding the complexed antibody; incubating the test mixture tube and negative control mixture tube for a time sufficient for binding of the antibody detection reagent and the complexed antibody complexes; separating the complexed antibody associated with the antibody detection reagent from unbound antibody detection reagent in the test mixture tube and negative control tube; and determining the amount of thrombospondin present on resting platelets in the test mixture tube and the negative control mixture tube, wherein the level of restin platelet thrombospondin is determined by subtracting the amount of complexed antibody present in the negative control tube from the amount of complexed antibody in the test mixture tube.

Such determinations are well-known to those of ordinary skill in the art of practicing radioligand binding assays or flow cytometric assays given the above protocol. A patient with an elevated level of resting platelet thrombospondin is predicted to be at risk for a thrombotic event.

Again, an elevated level of thrombospondin is defined as greater than about 200 molecules of thrombospondin per resting platelet or a level of more than 3-5% of maximal binding expected to the high affinity, cation-independent TSP receptor.

Most preferably, the level of thrombospondin per resting platelet would be greater than about 250 molecules per resting platelet by the radioligand binding assay or 5% TSP-positive resting platelets. Additionally, the assay values are to be corrected as to subtract readings of thrombospondin contributed by nonspecific binding, i.e. that reading obtained with the negative test mixture tube.

In the above described method, the antibody capable of binding thrombospondin on resting platlets is a monoclonal antibody. Most preferably, the detection of the described monoclonal antibody is by means of an antibody detection reagent such as fluorescent carboxylated microspheres coated with protein A or any other protein capable of binding specifically to the monoclonal antibody, and is to be used in the flow cytometric detection assay described above.

Although less sensitive, fluorescent labeled anti-IgG antibody or protein A may be used as an antibody detection reagent in place of microspheres. Alternatively, monoclonal antibody may be directly labeled with a fluorochome such as fluorescein, Texas Red, phycoerythrin, or rhodamine and used directly to detect the presence of surface-TSP bound to resting platelets by flow cytometry.

The Inventors' preliminary results using flow cytometry indicate that this method is more that 100 times more sensitive than the $\beta$TG release assay in the detection of platelet activation by thrombin in vitro (Example 9). When fluorescein labeled mouse anti-IgG is substituted for protein A-coated fluorescent microbeads, the assay is less sensitive, but is still 20 times more sensitive than the $\beta$TG assay in the detection of surface TSP on the resting platelet population (FIG. 8).

A method has also been devised whereby thrombospondin present on resting platelets may be determined through direct radioligand binding methods. Using such a technique, the method of determining a patient at risk of a thrombotic event is accomplished through determining the level of thrombospondin on resting platelets in a blood sample from the patient. The platelet sample is to be isolated and fixed as described herein. The patient platelet sample is then incubated with an amount of radiolabeled antibody which is sufficient to completely bind >99% of the surface TSP present in the patient sample. After allowing a sufficient time for binding of antibody to platelet surface TSP (about 60 min at room temperature), the test mixture (50 $\mu$l) is layered over a 300 $\mu$l cushion of 20% sucrose (w/w) and centrifuged for 5 min in a microfuge. The microfuge tube tip containing the labeled platelet pellet is cut off with a razor blade and the radioactivity determined in a gamma counter. Non-specific binding is determined by adding a sufficient amount of purified TSP to the radiolabeled antibody or excess unlabelled antibody prior to assay.

This inactivated antibody mixture is substituted for active monoclonal antibody in a second negative control test mixture tube and processed as above. The radioactivity associated with the platelet pellet (negative control) is subtracted from that associated with the test mixture tube yeilding the true amount of specific binding. The amount of radioactivity is then converted by calculation to the equivalent number of molecules of surface TSP per platelet present in the test patient sample. A value of more than 200, or more preferably more than 250, TSP molecules per resting platelet is diagnostic for a patient at risk of a thrombotic event.

In addition to the methods described above, the Inventors have also devised a thrombotic prediagnostic method assay based on a magnetic bead assay, to measure resting platelet thrombospondin to prediagnose patients at risk of a thrombotic event. This method comprises: obtaining an anticoagulated patient blood sample; separating platelets from the patient blood sample to provide a platelet test sample; exposing the platelet test sample to an antibody capable of binding to TSP present on resting platelets in the platelet test sample; incubating the antibody and platelet test sample a sufficient amount of time to allow the formation of antibody-resting platelet complexes to form a platelet antibody complexed sample; exposing the platelet antibody complexed sample complexes to a known amount of magnetic microspheres capable of binding an antibody-resting-platelet complex; incubating the antibody-resting-platelet for a sufficient time to allow binding of the microspheres to the antibody-resting-platelet complexes to form antibody-resting-platelet microsphere complexes; separating out the antibody-resting-platelet microsphere complexes from free platelets in the platelet test sample; and determining a percentage of free platelets that remain in the test sample and a percentage of platelet antibody microspheres platelets; wherein the difference between the percentage of free platelets and the platelets existing as as microbead-bound platelet complexes indicates the percentage of resting-platelet associated thrombospondin in the patient blood sample.

As a radioligand binding assay, a particularly preferred embodiment of the claimed diagnostic kit for prediagnosing a thrombotic event in vivo comprises a container means adapted to receive at least three carrier means; a first container means comprising an antibody capable of binding with thrombospondin on resting platelets; a second container means comprising thrombospondin; and a third container means comprising an antibody detection reagent.

In an even more preferred embodiment of the claimed diagnostic kits for flow cytometric, radioimmunoassay or magnetic bead assay, the antibody is further defined as a monoclonal antibody capable of binding with thrombospondin on resting platelets. Most particularly, the monoclonal antibody is the antibody F19D-2, which is available in Inventors' laboratory. In an especially preferred embodiment of the described kit, the monoclonal antibody is that monoclonal antibody deposited with the American Type Tissue Culture collection, having the accession number, ATCC #HB 10516.

In a most preferred embodiment of the described diagnostic kit for radioligand binding assay, the kit's first container means is further defined as comprising an $^{125}I$ labeled-monoclonal antibody capable of binding to thrombospondin present on TSP surface receptors of resting platelets.

Employing the methods or diagnostic kit disclosed in the present application, a thrombotic event may be predicted independent of how small the percentage of circulating "stimulated" platelets in a patient sample is.

The present invention also includes a diagnostic kit useful for the prediagnosis of persons at risk for a thrombotic event. The kit of the present invention may comprise those components necessary for either a flow cytometric assay, radioimmunoassay or for a magnetobead assay determination of resting platelet thrombospondin. As a flow cytometric assay, a most particularly preferred embodiment of the diagnostic kit for prediagnosing a thrombotic event in vivo comprises a carrier means adapted to receive at least three container means in close confinement therewith. A preferred embodiment of the kit comprises a first container means comprising an antibody capable of binding with thrombospondin on resting platelets; a second container means comprising a second antibody of isotype and species origin identical to the antibody capable of binding TSP but which does not itself bind to TSP; and a third container means comprising an antibody detection reagent. By way of example, a detection reagent may comprise a fluorescent antibody detection reagent such as an anti-IgG antibody or other IgG binding molecule labeled with a fluorochrome suitable for use with a flow cytometer. By way of example, the antibody detecting reagent is an anti-IgG antibody labeled with fluorescine, phycoerythrin, or rhodamine.

The kit may also optionally include a multiwell microtiter plate and a fourth container means comprising a solution of 20% sucrose; a fifth container means comprising a solution of 0.33 uM 30 fluorescent phallodian dissolved in a buffer containing 200 μg/ml lysolethicin, 8% formaldehyde and 0.1 M Na phosphate buffer; a sixth container comprising a blood collection container containing an anticoagulant solution; and a printed insert sheet with complete instructions for use.

In an even more preferred embodiment of the claimed diagnostic kit for flow cytometric assay, the fluorescent antibody detection reagent is further defined as flourescent microspheres coated with protein A.

In the magnetic bead assay embodiment of the diagnostic kit, the kit should include an antibody detecting reagent comprising anti-IgG-coated magnetobeads. A sufficient volume to add to all test samples and control samples of the assay should be included.

In a preferred embodiment, the biological sample is a human blood sample comprising resting platelets prepared according to the disclosed methods. The human platelet test sample is then used for detecting the presence of thrombospondin on the resting I5 platelet surfaces in a method for prediagnosing a thrombotic event. The human platelet blood sample is also used in the diagnostic kit described herein for measuring thrombospondin.

It is to be understood that other utilities and advantages of modifications of the specifically described aspects of the present invention are embraced within the scope of the following claims.

The following Examples 1-11 are presented only to describe preferred embodiments and utilities of the present invention, and are not meant to limit the scope of the present invention unless specifically indicated otherwise in the claims appended hereto.

Example 1 —Thrombospondin Isolation

Example 2 —Preparation of Anti-Thrombospondin Monoclonal Antibodies

Example 3 —Platelet Isolation, Stimulation and Fixation

Example 4 —Platelet-rich Plasma Production and Fixation

Example 5 —Platelet Magnasort Assay with Magnetobeads

Example 6 —Comparative Study Platelet Interaction with anti-TSP antibodies F19D-2 —Precipitation of Cells with a Second Antibody/TSP-1 Antibody vs. F19D-2 Antibody Example 7 —Flow cytometry analysis of resting platelet thrombospondin Example 8 —Radioimmunoassay Detection of TSP in a Biological Sample Example 9 —Enhanced Flow Cytometeric Analysis of Resting Platelet Thrombospondin Example 10 —Proposed in vivo Human Prediction of Thrombotic events using Flow Cytometry.

Example 11 —Proposed diagnostic kit for predicting thrombosis.

EXAMPLE 1

Thromobospondin Isolation

Exogenous sources of thrombospondin (TSP) include cells that synthesize and express TSP on their surfaces, the matrices produced by such cells, or platelets that have released TSP into the microenvironment. However, plasma does not constitute a significant source of TSP. While thrombospondin (TSP) may be obtained from any number of biological sources, as well as from several available commercial sources, in the presently disclosed methods and diagnostic kits with acceptable results, the most preferred source of thrombospondin is from fresh human platelets.

A particularly preferred method of obtaining and purifying thrombospondin from a fresh sample of platelets is generally by the method described by Lawler and coworkers[26]. The Lawler et al is specifically incorporated herein by reference for the purpose of detailing one general protocol for isolating thrombospondin from platelets only.

In brief, fresh human platelets (25 U) were stimulated with thrombin at 3 U/ml. Released TSP was separated from whole cells by centrifugation, and the TSP-containing supernatant was applied to a heparin-Sepharose (Pharmacia Fine Chemicals, Picataway, NJ) column. TSP was eluted using an NaCl gradient (with 0.45 mol/L NaCl, 2 mM Ca+2Cl,0.02 M TrisHCl, pH 7.2). The TSP-containing fractions were pooled based on concentration and stored frozen at $-70°$ C. The typical yield of TSP was 1 mg from each unit of platelets processed.

The purity of the thrombospondin (TSP) preparation was greater than 95 percent as determined by sodium dodecyl sulfatepolyacrylamide gel electrophoresis (SDS-PAGE) analysis.

EXAMPLE 2

Preparation of Anti-Thrombospondin Monoclonal Antibodies

The following example is presented to provide the most preferred method by which an anti-TSP monoclonal antibody is to be obtained. This particular monoclonal antibody has binding affinity for TSP on the surface and resting platelets. The anti-TSP monoclonal antibody is also a most preferred antibody to be used as a reagent in the described methods and kits. Preliminary results indicate that the monoclonal antibodies prepared according to the following method have the unique distinguishing characteristic of preferentially binding primarily only that thrombospondin present on the surface receptors of resting platelets, while being essentially free of binding affinity for thrombospondin present of the surface of activated platelets.

Hybridoma cell lines secreting antibody specific for thrombospondin were produced according to the following protocol. 3 month-old female Balb/c mice where immunized with 3 monthly (30 day, 60 day and 90 day) interperitoneal injections of 10 μg antigen (0.30 ml) emulsified in equal volume of Freund's complete (1×) and incomplete (2×) adjuvant. Three days prior to fusion, the immunized mouse was given 10 μg antigen (0.15 ml) intravenously by injection into the tail vein. Spleen cells from immunized mice were fused with SP2/0-AG-14 (Sp2) myeloma cells in the presence of 50% polyethylene glycol, pH 8.0 according to the protocol of Galfre and Milstein[2].

The mixture of fused and normal cells were diluted out into 120 ml of RPMI-1640 containing 2 mM glutamine and 15% fetal calf serum and 0.1 ml of this mixture was plated out into each well of 12-96 well microtiter plates. Following an initial incubation period of 16-18 hours, 0.1 ml of RPMI-1640 containing 2×concentrated HAT (Sigma) was added to each well. The growing hybridomas were given additional 0.1 ml culture medium (minus HAT) six days after the initial plating and culture supernatants (0.05-0.1 ml) tested for specific antibody to the immunizing antigen by an ELISA technique.

Cell cultures from wells with demonstrated antibody in their supernatants were cloned 2× by the limiting dilution technique. Eight clones originating from different wells were arbitrarily selected for antibody production, in ascites fluid, in as many as groups of 5 mice. The original cell lines representing positive wells, and clones from selected wells, were stored at $-135°$ C.

Cell line F19D-2 (ATCC HB 10516) is a hybridoma that was prepared according to the method of this Example 2. A hybridoma prepared according to the above method results in a hybridoma which produces an anti-thrombospondin monoclonal antibody capable of immunologically binding thrombospondin present on the surface of resting platelets. The anti-resting-platelet thrombospondin monoclonal antibody was determined to be an IgG1 by isotyping.

EXAMPLE 3

Platelet Isolation, Stimulation and Fixation

The present experiment was performed to demonstrate the increased sensitivity of TSP-platelet surface expression, as compared to measures of βTG secretion, in response to increasing thrombin concentrations. The βTG secretion was measured using a commercially available kit as described in [36] and according to the manufacturers instructions (Amersham, UK). The extent of antibody binding of the anti-thrombospondin antibody for thrombospondin present on paraformaldehyde-fixed samples of resting platelets is compared to βTG secretion measured by a commercial RIA kit. A βTG RIA is to be performed on supernatants obtained and stored frozen from each tube of "thrombin" stimulated platelets as well as unstimulated controls.

Isolation of platelets from a patient sample of 90 ml blood is accomplished by the following sequence of steps:

Isolation:

1. Collect 90 ml of blood in 15 ml of acid-citrate-dextrose containing 90 µl of PGEI (Sigma, St.Louis, MO) at 10 u/ml and theophylline (Sigma, St.Louis) at 10 mM.
2. Spinning down so as to separate out red blood cells and white blood cells at 1100 rpm for 20 minutes at 22° C.; save supernatant;
3. Spinning down platelets from the supernatant at 2400 rpm for 15 minutes at 22° C.
4. Resuspending the platelet pellet in 1 ml of Tyrode's, pH 7.2 with 1 mg/ml BSA.
5. Loading the resuspended pellet on Sepharose-CL-2B (Pharmacia Fine Chemicals, Piscataway, NJ) column.
6. Collecting 3.5 ml of cells from eluate of the column. Count platelets with Coulter electronic cell counter: Adjust to concentration of $5 \times 10^8$ cell/ml with Tyrode's medium.

Using the isolated platelets obtained from the above isolation, the stimulation of platelets is accomplished according to the following general protocol.

Stimulation

1. Obtaining 1 ml of the isolated platelets ($5 \times 10^8$ cells/ml); adding 25 µl. 0.2 M EDTA; adding serial dilutions of thrombin such that the highest final concentration is 0.25 u/ml and the lowest final concentration is 0.0005 u/ml; incubate 5 minutes at 22° C.; adding an excess of PPACK (Cabiochem, La Jolla, CA) to inactivate the thrombin.

Fixation of Platelets

Stimulated platelets obtained from this procedure were then fixed in paraformaldyhyde according to the following protocol. Fixed platelets were then used in the variously described diagnostic methods and kits for the measurement of resting platelet-(receptor)-associated thrombospondin.

|   | Platelets | 4% Paraformaldehyde | Incubation (30 min/22° C.) | 20 mM NH4Cl in in TBS pH 7.2 |
|---|---|---|---|---|
| 1. | 1.09 ml. | 138 µl. | — | 1240 |
| 2. | 1.09 ml. | 138 µl. | — | 1240 |
| 3. | 1.09 ml. | 138 µl. | — | 1240 |
| 4. | 1.09 ml. | 138 µl. | — | 1240 |
| 5. | 1.09 ml. | 138 µl. | — | 1240 |
| 6. | 1.09 ml. | 138 µl. | — | 1240 |
| 7. | 1.09 ml. | 138 µl. | — | 1240 |
| 8. | 1.09 ml. | 138 µl. | — | 1240 |

The platelets were spun down at 2300 rpm/22° C. for 5 minutes. The supernatant was then removed and saved for βTG RIA. The cells were then washed twice with Tyrode's buffer with 1mg/ml BSA.

Platelets are fixed to preserve the platelet samples and to avoid spontaneous activation or other physiological changes in the state of the platelet sample which could occur during subsequent manipulations.

EXAMPLE 4

Platelet-Rich Plasma Production and Fixation

A simplified method for preparing a platelet test sample was used for experiments not requiring the addition of thrombin to produce controlled levels of platelet activation. Specifically, this procedure was employed to address the issue of normal baseline levels on the surface of resting platelets obtained from both control donors and cardiovascular patients.

1. 5 ml of blood was collected into a tube containing 825 µl of acid-citrate-dextrose and 525 µl of PGE1 at 10 u/ml and theophylline at 10 mM. The blood was spun at 800 rpm for 10 minutes to produce a platelet-rich plasma sample.
2. To each 250 µl of platelet-rich plasma, 32 µl of 4% paraformaldehyde was added for 30 minutes at 22° C. Following the incubation, 282 µl of 20 mM NH4Cl in 0.45 M NaCl, 20 mM Tris-HCl, pH 7.6, was added. The sample was incubated for 5 minutes and microfuged in a Beckman Model E microfuge (Beckman Instruments, Palo Alto, CA) for 5 seconds. The supernatant was saved for βTG RIA for a comparison of the two methods in terms of sensitivity. In addition, a sample of the platelets was also reserved to determine the total possible quantity of βTG per sample so that the percentage of total βTG released in any given sample could be calculated.
3. The % of total βTG secretion was then compared to the % of platelets expressing TSP. If the larger portion of resting cells was expressing TSP from the few activated platelets, the % of βTG secretion will be less than the % of TSP positive cells.

EXAMPLE 5

Platelet Magnasort Assay With Magnetic Beads

The present experiment is provided to demonstrate another of the methods by which TSP on resting platelets may be quantitated. magnetic beads are the laboratory vehicle of choice in that they may be used in a quick and easy antigen-detection system. For the purpose of this invention, magnetic beads are coated with anti-mouse IgG. Magnetic beads coated with anti-mouse IgG were obtained from a commercial source (New England Nuclear, Boston, MA). The anti-mouse IgG-coated magnetic beads are then exposed to anti-TSP antibody. The fixed sample of platelets is then added. Bound platelets (i.e., resting platelets with TSP on the surface) may then be easily and quickly drawn down to the bottom of the reaction plate by placing the plate on a magnetic plate (New England Nuclear, Boston, MA), and the number of the magnetic beads with any associated platelets so "drawn down" by the magnetization process used as an indication of the amount of TSP on the resting platelets. While the present experiment provides a method for measuring TSP on resting platelets, stimulated platelets were run in the present experiment with magnetic beads in order to determine if slight increases in platelet activation (as induced by thrombin) could be detected by this assay method.

Platelets used in this assay were isolated, stimulated and fixed as described in Example 3. The cells (100 µl) were incubated with FI9D-2 ascites at a 1/100 dilution. The cells were incubated for 10 minutes with continuous shaking at 22° C. prior to a sample being taken for a cell count and the subsequent addition of anti-mouse coated magnetic beads (50 µl). After another 10 minute incubation, the 96 well plate was placed upon a large magnetic plate while shaking. When the supernatant appeared clear (no beads still floating), another 10 µl aliquot was counted in a Coulter Counter to determine the number of cells remaining in suspension.

The difference between cell counts prior to pelleting of the magnetic beads compared to the cell counts after the pelleting of the magnetic beads, was used to determine the extent of TSP surface expression on resting platelets. The fewer cells left in suspension, the greater the extent of TSP surface expression. The pelleted cells had TSP on their surface which interacted with the F19D-2 antibody and subsequently bound to the anti-mouse bead-associated antibody. To determine specific binding, the monclonal antibody was interacted with purified TSP prior to the addition of the antibody to the cells. This preincubation bound most of the antibody, thus the antibody was unable to interact with platelet surface bound TSP.

The amount of residual binding in the presence of excess free TSP was subtracted from the binding in the absence of excess soluble TSP to determine the specific TSP platelet surface expression. The results are displayed graphically in FIG. 5. In addition, if an antibody which binds to both resting and stimulated platelets was used instead of F19D-2, 100% of the cells were pelleted in the assay, as would be expected.

EXAMPLE 6

Comparative Study of TSP1—1 vs. F19D-2

The following example is provided to compare the TSP1—1 vs. F19D-2 anti-thrombospondin antibody affinity, sensitivity and specificity of resting platelets. The results of this comparative antibody study demonstrate that the anti-thrombospondin monoclonal antibody produced by hybridoma clone F19D-2 (ATCC #HB 10516) has a comparable sensitivity and specificity for thrombospondin on resting platelet surfaces as the TSP1—1 antibody produced by anti-thrombospondin clone 14E7 (ATCC #HB 8680).

The present experiment was conducted to compare the specificity of two different antibodies for thrombospondin present on the anti-thrombospondin antibody for TSP. 60% of the platelets were determined to have TSP on their surfaces (resting and activated platelets).

Platelets were first isolated, stimulated and fixed with paraformaldehyde as described in Example 3. The F19D-2 antibody is the same antibody as that described in Example 2. The experiment was conducted as described in Example 5, except samples were incubated with either F19D-2 or TSP1—1 (at a final concentration of 1/100).

This example illustrates that both the F19D-2 and TSP1—1 antibody may be used in the described assays to monitor TSP expression on the surface of platelets. The percent of cells pelleted by the two antibodies at various thrombin concentrations are tabulated below.

| | Thrombin Concentration (u/ml final) | % Cells Pelleted F19D-2 | TSP1-1 |
|---|---|---|---|
| 1. | .01 | 45.1 | 62.2 |
| 2. | .001 | 12.7 | 37.3 |
| 3. | .0001 | 0 | 7.7 |
| 4. | .00001 | 0 | 0 |

These results are presented graphically in FIG. 6.

EXAMPLE 7

Flow Cytometer Analysis of Resting Platelet Thrombospondin

The following example demonstrates the adaptability of using flow cytometry to detect platelet surface associated thrombospondin. FIGS. 7 and 8 demonstrate actual fluorescein labeled platelets obtained in these studies.

The present example is presented to outline a general method by which the described detection and quantitation of thrombospondin on resting platelets may be accomplished through fluorescent antibody tags with flow cytometry. The assay described in this example demonstrates the interaction of a preparation of stimulated platelets with anti-TSP Fab fragment antibody (rabbit 2166) and anti-rabbit IgG-Fluorescein antibody.

In general, the present method comprises first preparing a platelet sample as described in Example 3. Platelets were isolated, stimulated, and fixed according to Example 3. Anti-TSP Fab rabbit 2116 antibody was prepared at a concentration of 5.78 mg/ml. The cells were then indirectly stained with a rabbit anti-TSP polyclonal Fab fragment, followed by anti-rabbit IgG-Fluorescein. This procedure is presented in step-by-step fashion below:

1. Platelets were prepared according to Example 3.
2. The fixed platelet samples (1 ml) were incubated for 30 minutes at 37° C. with 10 μl of a 1/10 dilution of the Fab. The cells were spun down and resuspended in 50 μl of a 1/100 dilution of the fluoresceinated anti-rabbit IgG (original concentration of 1mg/ml). Following a 30 minute incubation at 37° C., the cells were washed with 500 μl of Tyrode's twice. The platelets were finally resuspended in 500 μl of Tyrode's.
3. The samples were analyzed by flow cytometry for relative fluorescent intensity. Relative fluorescent intensity may be measured utilizing methods to those skilled in the art of flow cytometry.
4. The resulting data was subjected to a subtraction analysis to determine the increase in TSP positive cells with increasing thrombin concentration (and therefore increasing platelet activation).
5. The "saved" supernatant samples from the fixed cells were assayed for βTG secretion utilizing a commercial RIA kit for βTG. The percent of cells positive for activation (as determined by % total βTG release) was compared to the percent cells positive for TSP surface expression at each thrombin concentration. The % cells positive for TSP surface expression at low thrombin concentrations (and thus low levels of platelet activation) measured according to the Inventors' described methods far exceeded the % cells positive for βTG secretion.

This example demonstrates that TSP released from the smaller number of cells also secreting βTG (βTG and TSP are compartmentalized in the same platelet granules) is interacting with a larger portion of cells than would be expected: and this population of platelets is the resting platelet component.

| Thrombin Concentration final (u/ml) | % βTG POSITIVE | % TSP POSITIVE |
|---|---|---|
| No PGE1/theo | 10.0 | 10.0 |
| 0.0005 | 10.0 | 21.8 |
| 0.001 | 11.0 | 27.6 |

-continued

| Thrombin Concentration final (u/ml) | % βTG POSITIVE | % TSP POSITIVE |
| --- | --- | --- |
| 0.002 | 11.0 | 34.7 |
| 0.004 | 12.0 | 42.2 |
| 0.008 | 13.0 | 51.8 |
| 0.015 | 27.0 | 57.3 |
| 0.03 | 22.0 | 63.5 |
| 0.06 | 28.0 | 73.6 |
| 0.12 | 54.0 | 78.9 |
| 0.25 | 40.0 | 83.1 |

This example also demonstrates that no change in activation by βTG RIA could be detected until a thrombin concentration of 0.015 μ/ml was present. In contrast, an increase in the % positive cells for TSP could be detected at the lowest thrombin concentration tested (at 0.005 u/ml). In fact, increased TSP expression was noted in unstimulated cells as compared to unstimulated cells in the continuous presence of platelet activation inhibitors (PGE1 and theophylline). The presently described methods are therefore advantageously capable of predicting a thrombotic event in a patient having less than an about 0.8% total circulating stimulated platelet level.

This example further suggests that TSP measurements are 15-20 fold more sensitive for limited platelet activation than a direct measure of activation (βTG RIA for activated platelet TSP). These findings provide strong support for the ability of TSP released from a small number of activated platelets to interact with a larger number of resting platelets thus, leading to the amplification required to develop a useful diagnostic test for detecting prethrombotic conditions. These data are presented graphically in FIG. 7.

The flow cytometer to be used in the analysis of resting platelet associated thrombospondin must first be adjusted so as to create a "window" of detection small enough to detect a 2 micron sized molecule. Such is necessary in order to detect the platelet, which is significantly smaller than most cells. These adjustments can be accomplished by anyone skilled in the art.

In a most preferred application of the described methods for the measurement of thrombospondin on resting platelets using the flow cytometry methods, the platelets will be isolated and fixed as described in Example 3. In this manner, blood need not be processed and analyzed immediately to avoid spontaneous activation in vitro.[13] Such greatly expands the clinical applicability of the claimed methods.

Fixed platelets can be studied by flow cytometry,[4]. The use of fixed platelets for the described monitoring of resting platelet associated thrombospondin is not expected to affect the binding of the described fluor-labeled anti-thrombospondin antibody to thrombospondin present on the surface of resting platelets.

EXAMPLE 8

Radioilabelled Antibody Determination of TSP on the Surface of Platelets

The present example is provided to demonstrate the applicability of the claimed invention for measuring platelet TSP immunologically using a standard radiolabelled ligand binding assay.[7]

Anti-TSP antibody was radiolabelled with $^{125}$I to a specific activity of about 0.5 microcuries per microgram by a modified chloramine-T procedure.[7] A radiolabelled ligand binding assay was performed substantially as described in Aiken et al.,[7] which is specifically incorporated herein by reference for such purpose.

Washed human platelets were incubated with an excess of radiolabelled monoclonal antibody. Following a 60 minute incubation, 50 μl aliquots of the incubation mixture were spun through a cushion of 20% sucrose for 2 minutes in a microfuge. The tips of the tube were amputated and counted to determine the quantity of radiolabelled antibody associated with the cells.

From the known specific activity of radiolabelled antibody, the molecules of antibody associated per cell was determined. Typically, less than 200 molecules of antibody associate with each platelet in the absence of thrombin if the cells are maintained in appropriate platelet inhibitors (PGE1 and theophylline). Levels over this amount may signal a predisposition to thrombosis.

Figure 1:
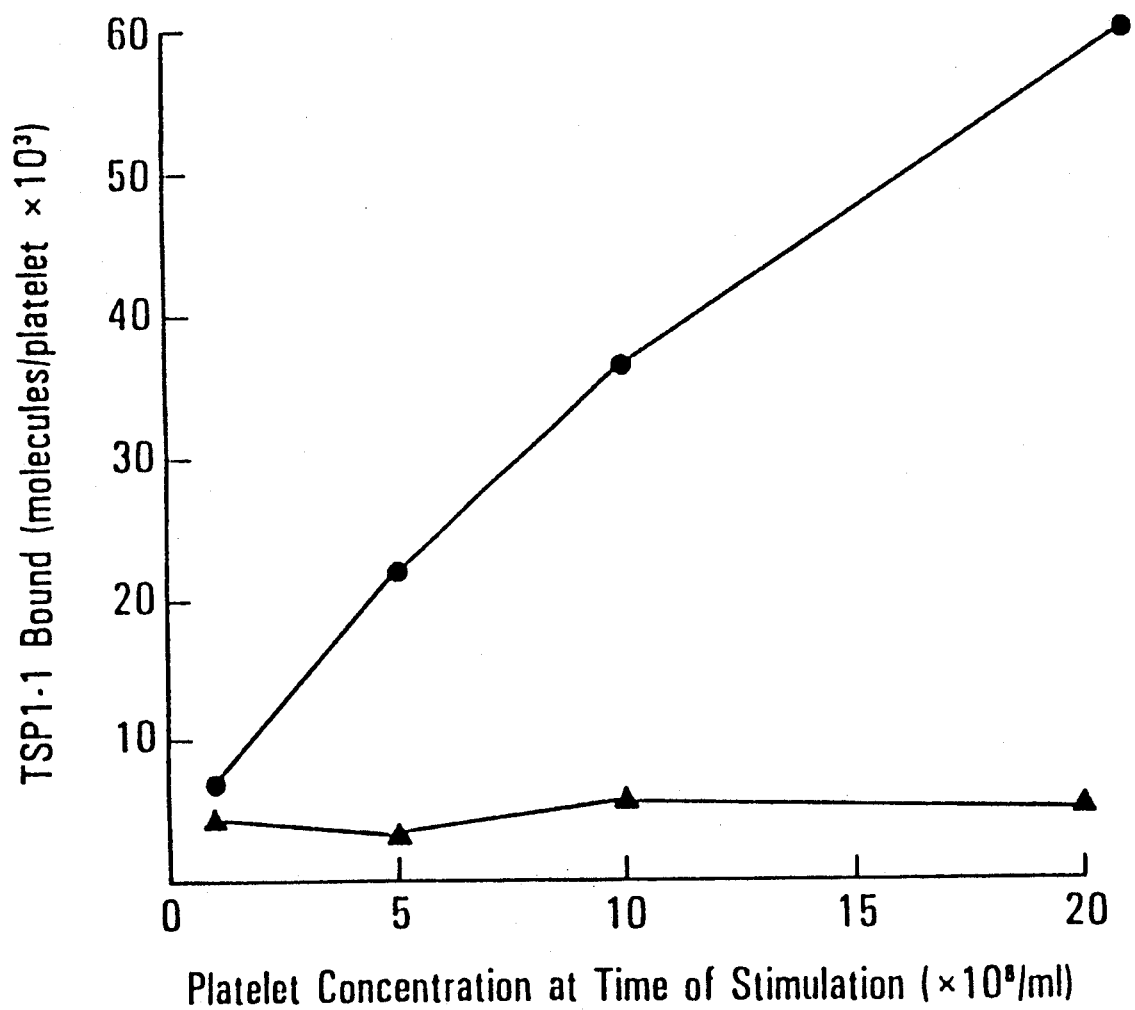
FIG. 1 —The expression of TSP on the surface of resting platelets is mediated by a high affinity receptor which is saturated at very low levels of TSP. Platelets at varying concentrations were stimulated with thrombin (0.25u/ml;Armour Pharmaceuticals, Kankeekee, IL) for 10 minutes prior to paraformaldehyde fixation. The fixed cells were then centrifuged and resuspended in Tyrode's buffer at a final concentration of 2 $10^8$/ml in the assay. The cells were incubated with a saturating concentration of $^{125}$I-TSP1—(a TSP specific monoclonal antibody) for 60 minutes. Following this incubation the platelets were centrifuged through a 20% sucrose cushion and the molecules of TSP1—1 bound was calculated. The TSP content of platelets is 20μg/$10^9$ cells. Based on this it is clear that the divalent ion-independent TSP receptor which is present on resting cells is saturated at a TSP concentration of 4nM. This is characteristic of high affinity receptors.[7]
Figure 2:
FIG. 2—Plasmin (KabiVitrum, Stockholm, Sweden) was added to $^{125}$I-TSP (1 unit/7μgof TSP) in the presence of 2mM Ca. After 2.5 hours at 37° C. pA-PMSF was added to inactivate the enzyme. Either the digest or intact TSP was then incubated with washed human platelets at 2×$10^8$/ml in the presence of 2mM Ca. The final concentration of label was 20nM. After a 30 minute incubation, the platelets were pelleted through 20% sucrose and extracted with Laemmli sample buffer.[81] The extracts were reduced with 2% beta-mercaptoethanol and applied to a 10% Laemmli slab gel.[81]

While the above described example was conducted with TSP1—1 and freshly prepared non-fixed cells7, other anti-thrombospondin antibodies give similar results, and fixation is only useful to prolong the time period during which the measurements can be made without spontaneous activation. The results of this type of assay with fixed platelets and radiolabelled F19D-2 as the reporter molecule are represented graphically in FIG. 1.

EXAMPLE 9

Enhanced Flow Cytomete Analysis of Resting Platelet Thrombospondin

The following example is presented to demonstrate if the high affinity interaction between TSP and the platelet surface occurs in the presence of plasma proteins which may potentially interfer. Another main objective of the present example was to increase the sensitivity of the assay by utilizing an extremely sensitive fluorescent secondary marker.

The results indicate that TSP does interact with resting platelets in the presence of plasma proteins, such as fibrinogen. In addition, the secondary reporter for TSP surface expression was much more sensitive than in the previously described examples.

1. Blood (90 ml) was drawn into 15 ml of acid citrate dextrose. The whole blood was centrifuged at 800 ×g at 22° C. for 20 minutes to obtain a platelet rich plasma.
2. 4 ml of plasma was placed in each of 4 tubes. Three of the tubes were subjected to mechanical aggitation (plasma was drawn into a plastic syringe and ejected back into the tube). Mechanical aggitation was performed to give extremely minimal platelet activation levels (low levels of thrombin could not be used as with washed platelets due to the presence of fibrinogen in plasma which would clot under these conditions).
3. 420 μl of PGEI and theophylline (10u/ml and 10mM respectively) was added to all 4 tubes. This was followed by 552 μl of 4% paraformaldehyde. After 30 minutes at 22° C., 4972 μl of 20mM NH4Cl was added. The cells were spun at 2200 rpm for 15 minutes. The supernatants and a sample of untreated plasma were saved for βTG RIA. The cells were resuspended in Tyrode's (1 ml) and stored at 4° C.
4. 200 μl of each sample was microfuged and resuspended in 200 μl of 20mM Tris, 0.45M NaCl, 2mM CaCl, pH 7.6 containing a 1/100 dilution of F19D-2. Alternatively, 200 μl of the samples were resuspended in this buffer containing F19D-2 at 1/100 and TSP at a concentration of 0.398 mg/ml for a specificity block. Following a 30 minute incubation at 22° C., a 10 μl aliquot of 1 micron fluorescently dyed beads coated with Protein-A (Polysciences, Warrington, PA) was added. After 30 minutes at 22° C., 100 μl aliquots were layered on 20% sucrose in Tyrode's and spun in a microfuge for two minutes. This procedure was used to exclude most of the unbound beads which remained in the sucrose while the platelets were pelleted. The sucrose was aspirated off and the platelets resuspended in 50 μl of residual sucrose. 50 μl of 0.33 μm Rhodamine-phalloidon (Polysciences, Inc.) cocktail containing 200 μg lysolethicin, 8% formaldehyde in Na phosphate buffer (pH 7.2) was added for 5 minutes to stain filamentous actin (Howard et al. (1984), J. Cell. Biol. 98:1265-1271). This procedure allowed only the red stained platelets (and not free beads, debris, etc.) to be analyzed for green fluorescence by flow cytometry. The percent positive cells in the blocked samples were subtracted from their counterparts to determine the specific component of positive cells.

| Sample | % βTG Positive | % TSP Positive |
|---|---|---|
| No Disruption | 0.94 | 2.8 |
| Disruption #1 | 1.3 | 11.4 |
| Disruption #2 | 1.0 | 7.6 |
| Disruption #3 | 1.0 | 8.9 |

This example clearly demonstrates that TSP surface expression is a sensitive marker for platelet activation. Mechanical agitation prior to fixation resulted in a very small increase in measurable βTG secretion over the baseline undisrupted level (0.36%, 0.06%, and 0.06% respectively). In contrast, the increase in percent cells positive for TSP was quite dramatic (8.6%, 7.6%, and 6.1 respectively). Thus, the detection of platelet TSP surface expression by this assay method is 20-120 fold more sensitive than βTG measurements.

PROPHETIC EXAMPLE 10

Proposed In Vivo Human Prediction of Thrombotic Events

The present example outlines the procedure contemplated by the Inventors to be useful for the successful prediction of thrombogenic events in humans. The use of flow cytometry to accomplish this goal is presented as a method which is relatively rapid and easily incorporated into routine clinical hospital laboratories equipped with a flow cytometer to screen samples.

The Inventors intend to develop a test to prediagnose or identify individuals at risk of a thrombotic event in humans. In the development of this method, a "normal" standard against which to judge sample thrombospondin levels is being established from the determination of a mean TSP value from a panel of different blood platelet samples. The variability of TSP expressed on the surface of resting platelets observed from a number of human samples will be thus controlled for and a mean thrombospondin value determined to establish a mean resting platelet thrombospondin level from a pool of samples obtained from young healthy donors.

The Inventors will also determine the level of TSP expressed on the surface of platelets from individuals who have suffered a recent thrombotic episode or who may have a familial history of thrombotic disease. Individuals having recent thrombotic episodes are expected to have elevated levels of TSP expressed on the surface of their platelets for a short period of time, after which resting platelet thrombospondin levels return to prethrombosis levels, and new platelets become part of the circulation. Inventors plan to correlate the data collected with known diagnosis or familial history. It is postulated that a correlation will develop between this data and known diagnosis or familial history of the patient.

Residual blood samples from normal healthy donors or cardiology patients (approximately 5 ml) will be subjected to centrifugation to obtain platelet-rich plasma as described in Example 4. Most preferably, the TSP surface expression on these resting cells will then be determined by assays as described in Example 10 above.

While the identity of the patient may remain unknown, the diagnosis and/or pertinent familial history will be provided to the primary investigator, thus a correlation between increased TSP surface expression and recent thrombotic events or a familial history of thrombosis may be established.

The Inventors plan to establish the normal variation in TSP-platelet surface expression. The quantitative assay for TSP-platelet surface expression is described by Example 3 and Example 10 above.

In a most preferred embodiment of the presently claimed diagnostic and predictive methods for identifying a patient at risk of a thrombotic event, the method comprises the steps of: collecting a blood sample comprising platelets from the patient into a receptacle containing prostaglandin and theophylline; isolating the platelet-rich fraction from the blood sample; determining the amount of thrombospondin on the resting platelet; and identifying those blood samples having an elevated amount of thrombospondin on resting platelets. Patient samples identified as having an elevated level of thrombospondin on resting platelets would be indicative of a patient at risk of a thrombotic event. Most preferably, the blood sample should be collected in a receptacle which contains theophylline and prostaglandin. The inclusion of these ingredients will minimize artificial spontaneous platelet activation.

In preliminary studies, 15 normal donors have been tested by preparing a plasma sample as in Example 4 followed by the staining procedure described in Example 10. The results are presented graphically in FIG. 9. In 13 of the cases the test has been run twice while for the remaining two donors only a single test has been conducted to date. The thus far established mean value for normal healthy donors is 2.71% with a standard deviation of 3.65.

A limited number of patient samples have also been tested. Of the 8 patients known to have some degree of cardiovascular disease, 3 had more than 20% positive cells for TSP. These results are presented graphically in FIG. 9. This limited but ongoing study has given some insight into possible factors which may effect the test results. One of the normal donors had an elevation in platelet TSP levels (as compared to the first test) following a bleeding incident. It is highly likely that recent bleeding episodes will increase the expression of TSP on resting platelets for 5-7 days. In the future normal donors will be asked if they have had any recent bleeding. Of the cardio-vascular patients, the majority who have been taking anti-platelet drugs (ie. aspirin) tested within the normal range. This is not unanticipated:

however, this observation supports the need to know what regimin has been ordered for each patient.

PROPHETIC EXAMPLE 11

Proposed Diagnostic Kit for predicting Thrombosis

Any of the diagnostic and predictive methods described herein may be embodied in a conveniently packaged kit for the same purposes. For example, reagents necessary for performing a radioimmunoassay, a magnetic bead assay, or for performing a flow cytometric assay, as described in Inventors' prior examples may be incorporated into a kit form and used in the methods described to measure thrombospondin on the surface of resting platelets obtained from a patient sample.

The present example provides a detailed description of a particular diagnostic kit contemplated by the Inventors to be used in for predicting those persons at risk of a thrombotic event. More specifically, the kit may be advantageously used in predicting the risk of a thrombotic episode through the analysis of a patient's blood sample containing resting platelets.

The diagnostic kit provides those reagents necessary to detect the level of thrombospondin expressed on the surface of resting platelets in a biological sample, most preferably a human blood sample.

The present invention also includes a diagnostic kit useful for the prediagnosis of persons at risk for a thrombotic event. The kit of the present invention may comprise those components necessary for either a flow cytometric assay, radioimmunoassay or for a magnetic bead assay determination of resting platelet thrombospondin.

As a flow cytometric assay, a most particularly preferred embodiment of the diagnostic kit for prediagnosing a thrombotic event in vivo, the kit comprises a container means adapted to receive at least two carrier means in close confinement therewith; a first container means comprising an antibody capable of binding with thrombospondin on resting platelets; a second container means comprising thrombospondin or alternatively, an antibody of isotype and species origin identical to the antibody capable of binding TSP but which does not itself bind to TSP; and a third carrier means comprising a fluorescent antibody detection reagent.

The described kit may also optionally include a fourth container means comprising a sterile solution of 20% sucrose; a fifth container means comprising a solution 0.33 uM fluorescent phallodian dissolved in a buffer containing 200 μg/ml lysolethicin, 8% formaldehyde and 0.1 M Na phosphate buffer; a sixth container comprising a blood collection container containing an anticoagulant solution; a multiwell microtiter plate; and a printed insert sheet with complete instructions for use.

In a more preferred embodiment of the claimed diagnostic kit for flow cytometric assay, the antibody capable of binding thrombospondin present on resting platelets is a monoclonal antibody F19D-2 (ATCC #HB 10516).

In an even more preferred embodiment of the claimed diagnostic kit for flow cytometric assay, the fluorescent antibody detection reagent is further defined as flourescent microspheres coated with protein A (Polysciences, Warrington, PA).

Thrombospondin as part of the kit is most preferably that obtained or isolated from a preparation of human platelets as described in Example 1.

BIBLIOGRAPHY

1. Curtiss, et al. *J. Biol. Chem.*, 257:15213.
2. Jaffe et al. (1982), *Nature*, (London, England), 295(5846):246-8.
3. Wencel-Drake et al. (1984), *Am. J. Path.* (USA), 115(2):156-64.
4. Legrand et al. (1987), *Eur. J. Biochem.*, 171(1-2):3-93-9.
5. Aiken et al. (1987) *Blood* (USA), 69(1):58-64.
6. Aiken et al. (1986), *J. Clin. Invest.* (USA), 78:1713-1716.
7. Aiken et al. (1987), *Seminars in Thrombosis and Haemostasis*, 13(3):307-316.
8. Wolff et al. (1986), *J. Biol. Chem.* (USA), 21(15):6840-6.
9. Perlman et al. (1987), *Eur. J. Nucl. Med.* (Germany, West), 12(10):492-5.
10. Silverstein et al. (1987), J. Clin. Invest. (USA), 79(3):867-74.
11. McCrohan et al. (1987), *Thromb. Haemostasis*, 58(3):850-2.
12. Switalska et al. (1985), *J. Lab. Clin. Med.* (USA), 106(6):690-700.
13. Abrams et al. (1990), *Blood*, 75:128-138.
14. Tuszynski et al. (1988), *Blood*, 72(1):109-115
15. Kao et al. (1986), *Am. J. Clin. Pathol.* (USA), 86(3):317-23).
16. Plow et al. (1971), *J. Immunol.*, 107:1495.
17. Plow et al. (1986), *In: Biochemistry of Platelets*, Phillips and Shuman, eds., p. 226.
18. Goodman and Gilman, (1985), *The Pharmacological Basis of Therapeutics*, 7th ed. pp. 1338-62.
19. Harker et al., (1983), *Thromb. Haemost*, 50:22.
20. Saglio et al., (1982), *Blood*, 59:162.
21. W.P.O. No. 86-258293/39 - U.S. Pat. No.4610960, Mosher
22. W.P.O. No. 86-278726/42 - U.S. Pat. No. 4820505, Ginsberg
23. Shadle et al. (1984) *J. Cell Biol.* 99:2056-2057
24. Leung et al. (1984) *J. Clin. Invest.*, 74:1764-1772.
25. Gartner (1984), *Biochem. Biophys. Res. Commun.*, 124: 290-295.
26. Lawler et al. (1978), *J. Biol. Chem.*, 253:8607-16.
27. Kennedy et al. (1982), *Biabetes*, 31(3):52.
28. Boukerche et al. (1988) *Eur. J. Biochem.*, 171:383-392.
29. Kieffer et al. (1988) *Biochimica et Biophysica Acto*, 967:408-415
30. Gershlick, A.H., (1990) *Circulation*, 81(1):1-28, 1-34.
31. Frink et al. (1988) *Br. Heart J.*, 59:196-200.
32. Fuchs et al. (1987) *Am. J. Cardiol.*, 60:534-537.
33. George et al. (1984) *New England J. Med.*, 311:1084-98.
34. Lawler, J. (1986), *Blood*, 67:1197-1209.
35. Raugi et al. (1982), *J. Cell Biol.*, 95:351-54.
36. Nurden et al., (1974), *Br. J. Haematol.*, 28:233-253.
37. Shattil (1988), *In: Platelet Membrane Receptors: Biochem. Immun. and Path.*, p. 345.
38. Adelman (1987), *Blood*, 70:1362.
39. Cella et al., (1983), *Eu. J. Clin. Invest.*, 11:165.
40. O'Gara et al. In: Conn's Current Theraphy, R.E. Rakel, ed., (1991), pp. 255-284
41. Dupont "Magnasort" Assay
42. George et al., (1980), *J. Clin. Invest.*, 66:1-9.
43. Johnston et al., (1987), *Blood*, 69:1401.
44. Shattil et al., (1987), *Blood*, 70:307.

45. Yielding et al., (1987), unpublished observations.
46. Rouslati
47. Philips (1980) *J. Biol. Chem.*, 255:11629-11632.
48. George et al., (1986) *J. Clin Invest.*, 78:340-348.
49. Hourdeille et al., (1985), *Blood*, 65:912-920.
50. Asch et al., (1985), *Blood*, 66:926-934.
51. Badaracco et al., (1974), *Mayo Clin. Proc.*, 1:215
52. Barker et al. (1940), *Mayo Clin. Proc.*, 15:769.
53. Barker et al., (1941), *Mayo Clin Proc.*, 16:1.
54. Bennett et al., (1966), *J. Clin. Pathol.*, 19:241
55. Bensinger et al., (1970), *Blood*, 36:61.
56. Bolton et al., (1968), *Lancet*, 1:1336.
57. Vaitukaitis et al., (1971), *J. Clin. Endocrinol. Metab.*, 33:988-991.
58. Brown et al., (1980), *Clin. Chem.* in press.
59. Plow et al., (1985), *Blood*, 66:724-727.
60. Roberts et al., (1985), *J. Bio. Chem.*, 260:9405-9411.
61. Asch et al., (1987), *J. Clin. Invest.*, 79:1054-1061.
62. Kieffer et al., (1987), *Thromb. Haemost.*, 58:733a.
63. Bernstein et al., (1982), *J. Immunol.*, 128:876-881.
64. Leung et al., (1982) *J. Clin. Invest.*, 70:542-549.
65. Levy-Toledano et al., (1981), *J. Lab. Clin. Med.*, 98:831-848.
66. Nurden et al., (1982), *Blood*, 59:709-718.
67. Birembaut et al., *J. Histochem. Cytochem.*, 30:75-80.
68. Meyer et al., (1983), *Br. J. Haematol.*, 54:1-9.
69. Berndt et al., (1984), *Thromb. Res.*, 7:111-150.
70. Olsen et al., (1983), *Thromb. Res.*, 32:115-122.
71. Page et al. (1979), *Thromb. Haemost.*, 42:705-725.
72. McGregor, J.L. (ed.), In: Monoclonal Antibodies and Human Blood Platelets, Elsevier Science (1986), p. 1.
73. Ruggeri et al., In: Platelet Immunobiology Molecular and Clincial Aspects, Lippincott (1989) p. 235.
74. Roberts et al., (1972), *Am. J. Med.*, 52:425-443.
75. Haerem, J.W., (1972) *Atherosclerosis*, 15:199-213.
76. Falk, E., (1985), *Circulation*, 71:699-708.
77. Davies et al., (1986), *Circulation*, 73:418-427.
78. Gordon et al., (1973), *J. Clin Pathol.*, 26:958-962.
79. Haft et al., (1975), *Clin Res.*, 23:186A.
80. Howard et al. (1984), *J. Cell Biol.*, 98:1265-1271
81. Marguerie et al. (1980), *J. Biol. Chem.*, 255:154-161.
82. Coon, W., *Ann. Surg.*, 186(2):149-164.
83. Heart and Stroke Facts, (1991) American Heart Assoc., Dallas, TX

What is claimed is:

1. A method for early identification of a thrombotic event in a patient consisting essentially of obtaining a blood sample from a patient and isolating the platelets therein; monitoring the thrombospondin on the resting platelets in the sample; and identifying an early thrombotic event in a patient with elevated resting platelet thrombospondin.

2. The method of claim 1 wherein thrombospondin associated with resting platelets may be monitored by a radiolabeled ligand binding assay, a magnetic bead assay, or flow cytometry techniques.

3. The method of claim 1, wherein thrombospondin associated with resting platelets is detected by contacting a sample possibly containing resting platelet-associated thrombospondin with an antibody capable of binding thrombospondin on resting platelets.

4. The method of claim 1, wherein the resting platelets include a surface comprising thrombospondin receptors.

5. The method of claim 1, wherein the antibody binds to thrombospondin at thrombospondin receptors of the resting platelets.

6. The method of claim 1, wherein the antibody is produced by hybridoma ATCC #HB10516.

7. A method for identifying a patient at risk of a thrombotic event consisting essentially of monitoring resting platelet thrombospondin according to the steps of:
   acquiring blood samples from patients;
   obtaining platelet fractions from the blood samples;
   determining thrombospondin amounts on resting platelets of the platelet fractions; and
   identifying blood samples having an elevated amount of thrombospondin on resting platelets, wherein a patient blood sample identified as having an elevated level of thrombospondin on resting platelets indicates a patient at risk of a thrombotic event.

8. The method of claim 7, wherein an elevated level of thrombospondin on resting platelets comprises a number of resting platelet-associated thrombospondin molecules which is greater than an established normal range.

9. The method of claim 7 wherein an elevated level of thrombospondin on resting platelets comprises a number of resting platelet associated thrombospondin molecules of at least 200 molecules thrombospondin per resting platelet.

10. The method of claim 7, wherein an elevated level of thrombospondin on resting platelets comprises at least 250 molecules thrombospondin per resting platelet.

11. The method of claim 7, wherein identifying a patient having an elevated thrombospondin level is further defined as comprising:
   obtaining a blood sample from the patient to form a test sample comprising resting platelets;
   mixing a known quantity of the test sample with a known quantity of an antibody capable of binding thrombospondin on resting platelets to form a test mixture;
   maintaining the test mixture for a time period sufficient to allow the antibody to bind thrombospondin present on the resting platelet thrombospondin receptors to form a complexed antibody;
   separating the complexed antibody complexes from the test mixture;
   determining the level of thrombospondin on the resting platelets in the blood sample from the amount of complexed antibody present in the test mixture; and
   identifying a patient having an elevated level of thrombospondin on resting platelets as a level greater than about 200 molecules of thrombospondin per resting platelet;
wherein an elevated level of thrombospondin identified a patient at risk of a thrombotic event.

12. The method of claim 7, wherein thrombospondin on the resting platelets is present at resting platelet surface thrombospondin receptors.

13. The method of claim 7, wherein the patient is a human.

14. The method of claim 7, wherein the thrombogenic event is thrombosis, stroke, cardiovascular disease, deep venous thrombosis, pulmonary embolism, or myocardial infarction.

15. The method of claim 7, wherein the test mixture is to be maintained between about 30 minutes and about 90 minutes at about 22° C. or about 37° C.

16. A method for preventing a thrombotic event in a patient through the early detection of elevated levels of thrombospondin on resting platelets in a patient sample consisting essentially of:

obtaining a blood sample from the patient and isolating a platelet fraction from the sample;

determining the amount of thrombospondin associated with the resting platelets; and identifying a patient having an elevated level of thrombospondin on resting platelets; and administering to the identified patient a pharmacologically acceptable anti-thrombotic pharmaceutical agent.

17. A method of claim 16, wherein the antithrombotic pharmaceutical agent is heparin, acetylsalicyclic acid, or other anti-platelet agent effective in preventing platelet activation in vivo.

18. The method of claim 16, wherein identifying a patient having elevated resting platelet thrombospondin levels comprises:

determining the level of resting platelet thrombospondin in a patient sample;

comparing the patient level of resting platelet thrombospondin to a mean resting platelet thrombospondin level, wherein a mean resting platelet thrombospondin level comprises an average resting platelet thrombospondin level from a non-thrombotic population of patient samples, and wherein an elevated resting platelet thrombospondin level is identified as a patient thrombospondin level above the mean resting platelet thrombospondin level.

19. The method of claim 18 determining the level of resting platelet thrombospondin comprises the steps of:

preparing a platelet-rich plasma sample to provide a platelet-rich plasma sample comprising resting platelets;

exposing a known amount of the platelet-rich plasma sample to a known amount of an antibody capable of binding thrombospondin on resting platelets to form a test mixture tube;

preparing a second tube comprising a known amount of patient platelet-rich plasma and exposing the second tube to a known amount of an antibody rendered incapable of binding platelet surface thrombospondin on resting platelets, to form a negative control tube;

incubating the test mixture tube and the negative control tube a period of time sufficient to allow binding of thrombospondin present in the test mixture tube and the negative control tube to the antibody to form complexed antibody;

exposing the complexed antibody in the test mixture tube and the negative control tube to a sufficient quantity of an antibody detection reagent capable of binding the complexed antibody;

incubating the test mixture tube and negative control mixture tube for a time sufficient for binding of the antibody detection reagent and the complexed antibody;

separating the complexed antibody associated with the antibody detection reagent from unbound antibody detection reagent in the test mixture tube and negative control tube; and the amount of thrombospondin present on resting platelets in the test mixture tube and the negative control mixture tube;

wherein the level of resting platelet thrombospondin is determined by subtracting the amount of complexed antibody present in the negative control tube from the test amount of complexed antibody in the test mixture tube.

20. The method of claim 19 wherein the antibody is rendered incapable of binding thrombospondin on resting platelets is prepared by preincubating the antibody with sufficient purified thrombospondin to render it inactive.

21. The method of claim 18, wherein the antibody capable of binding thrombospondin on resting platelets is a monoclonal antibody.

22. The method of claim 21, wherein the monoclonal antibody is labeled with $I^{125}$.

23. The method of claim 21, wherein the monoclonal antibody is labeled with a fluorescent substance.

24. The method of claim 21, wherein the monoclonal antibody is labeled with an enzyme.

25. The method of claim 18, wherein the monoclonal antibody is detected with an antibody detection reagent;

26. The method of claim 25, wherein the antibody detection reagent is a substance capable of binding to the monoclonal antibody.

27. The method of claim 26, wherein the antibody detection reagent is a fluorescent microsphere coated with protein A or, alternatively, an antibody which binds to the monoclonal antibody.

28. The method of claim 26, wherein the antibody detection reagent is a magnetic microsphere coated with protein A or, alternatively, an antibody that binds to the monoclonal antibody.

29. The method of claim 26, wherein the antibody detection reagent is a fluorescent conjugate of protein A, or alternatively, an antibody that binds to the monoclonal antibody.

30. The method of claim 21, wherein the monoclonal antibody is produced by a hybridoma clone ATCC#HB10516.

31. A method for prediagnosing a thrombotic event in a patient consisting essentially of monitoring thrombospondin on resting platelets in a patient blood sample according to the steps of:

obtaining an anticoagulated patient blood sample;

separating platelets from the patient blood sample to provide a platelet test sample;

exposing the platelet test sample to an anti-thrombospondin antibody capable of binding to TSP receptor binding sites on resting platelets in the platelet test sample;

incubating the antibody and platelet test sample a sufficient amount of time to allow the formation of antibody-resting platelet complexes to form a platelet antibody complexed sample;

exposing the platelet antibody complexed sample to a known amount of magnetic microspheres capable of binding an antibody resting-platelet complex;

incubating the platelet test sample for a sufficient time to allow binding of the microspheres to the antibody-resting platelet complexes to form antibody-resting platelet microsphere complexes;

separating out the antibody-resting platelet microsphere complexes from free platelets in the platelet test sample; and determining a percentage of free platelets that remain in the test sample and a percentage of platelet-antibody-microsphere platelets;

wherein the difference between the percentage of free platelets and microbead-bound platelet complexes indicates the percentage of resting-platelet associated thrombospondin in the patient blood sample for use in a thrombotic prediagnostic method.

* * * * *